United States Patent

Bhatnagar et al.

[11] Patent Number: 5,527,919
[45] Date of Patent: Jun. 18, 1996

[54] PROCESS FOR THE PREPARATION OF 1-[(1,1'-BIPHENYL]-4-YL]-METHYL-1H-IMIDAZOLE-5-CARBOXYLIC ACIDS

[75] Inventors: Neerja Bhatnagar, Savigny Sur Orge; Jean Buendia, Le Perreux Sur Marne; Christine Griffoul, Rosny Sous Bois, all of France; Holger Heitsch, Hofheim; Adalbert Wagner, Hattersheim/Main, both of Germany

[73] Assignee: Roussel Uclaf, France

[21] Appl. No.: 177,153

[22] Filed: Jan. 4, 1994

[30] Foreign Application Priority Data

Oct. 19, 1993 [FR] France ................................. 93 12413

[51] Int. Cl.⁶ ..................... C07D 233/84; C07D 233/90
[52] U.S. Cl. ................. 548/250; 548/322.5; 548/343.5; 548/346.1; 548/343.1
[58] Field of Search ..................... 548/322.5, 344.5, 548/346.1, 250

[56] References Cited

FOREIGN PATENT DOCUMENTS 465368   1/1992   European Pat. Off. .
503162   9/1992   European Pat. Off. .

*Primary Examiner*—Jacqueline Haley
*Attorney, Agent, or Firm*—Bierman & Muserlian

[57] ABSTRACT

A novel process for the preparation of a compound of the formula

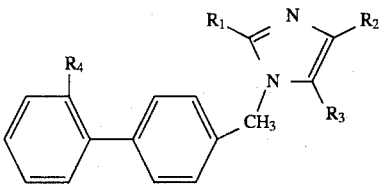

wherein $R_1$, $R_2$, $R_3$ and $R_4$ are defined in the text.

9 Claims, No Drawings

PROCESS FOR THE PREPARATION OF 1-[(1,1'-BIPHENYL]-4-YL]-METHYL-1H-IMIDAZOLE-5-CARBOXYLIC ACIDS

OBJECTS OF THE INVENTION

It is an object of the invention to provide a novel process for the preparation of a compound of formula I and novel intermediates.

This and other objects and advantages of the invention will become obvious from the following detailed description.

THE INVENTION

The novel process of the invention for the preparation of a compound of the formula

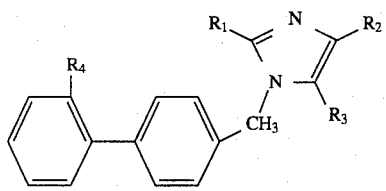

wherein $R_1$ is selected from the group consisting of alkyl, alkenyl, alkynyl and alkylthio of up to 10 carbon atoms and cycloalkyl of 3 to 7 carbon atoms, all optionally substituted, $R_2$ and $R_3$ are individually selected from the group consisting of:

a) hydrogen, halogen, —OH, —SH, acyl of an organic carboxylic acid of 1 to 7 carbon atoms, —$NO_2$, —CN, free, salified or esterified, carboxy and —$PO_3(R)_2$, b) —$(CH_2)_{m1}$—$S(O)_{m2}$—X—$R_{10}$, c) alkyl, alkenyl, alkoxy and optionally oxidized alkylthio of up to 6 carbon atoms optionally interrupted by at least one —O—, —S— or nitrogen and optionally substituted, d) optionally substituted phenyl, benzoyl and optionally oxidized phenylthio, e)

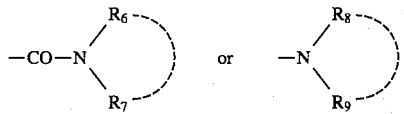

f) —S—S—$R_{12}$,

R is hydrogen or optionally substituted alkyl or phenyl, $m_1$ is an integer from 0 to 4, $m_2$ is an integer from 0 to 2, X is selected from the group consisting of a single bond, —NH—, —NHCO—, —NH—COO—, —N=CH—N—$R_{13}$ and —NHCONH—, $R_{10}$ and $R_{13}$ are individually selected from the group consisting of hydrogen, alkyl and alkenyl of up to 6 carbon atoms, cycloalkyl of 3 to 6 carbon atoms, optionally substituted phenyl and benzyl, pyridyl, nitropyridyl, pyrimidyl, tetrazolyl, diazolyl, piperidinyl, alkylpiperidinyl, thiazolyl, alkylthiazolyl, tetrahydrofuranyl and methyltetrahydrofuranyl; $R_6$ and $R_7$ or $R_8$ and $R_9$ are individually selected from the group consisting of hydrogen, amino acids, optionally substituted alkyl and alkenyl of up to 6 carbon atoms, optionally substituted phenyl, benzyl and phenethyl and —$(CH_2)_{m1}$—$S(O)_{m2}$—X—$R_{10}$ or $R_6$ and $R_7$ or $R_8$ and $R_9$ taken together with the nitrogen to which they are attached form a monocyclic ring of 5 to 7 ring members or condensed rings of 8 to 14 ring members, both optionally containing at least one heteroatom of the group consisting of —O—, —S— and nitrogen and optionally substituted with at least one member of the group consisting of halogen, —OH, —$NO_2$, alkyl and alkoxy of 1 to 6 carbon atoms, —$NH_2$, mono and dialkylamino of 1 to 6 carbon atoms and phenyl or $R_8$ and $R_9$ are individually acyl of an organic carboxylic acid of 1 to 6 carbon atoms or one of $R_8$ and $R_9$ is carbamoyl, alkoxylcarbonyl or benzyloxycarbonyl or $R_8$ and $R_9$ together with the nitrogen form phthalimido or succinimido, $R_{12}$ has the definitions of $R_2$ and $R_3$ except for amino or alkoxy with the proviso at least one of $R_2$ and $R_3$ is an optionally substituted alkoxy or —$(CH_2)_{m1}$—$S(O)_{m2}$—X—$R_{10}$, $R_4$ is selected from the group consisting of —$(CH_2)_{m1}$—$S(O)_{m2}$—X—$R_{10}$ as defined above, halogen, nitro, —$(CH_2)_{m1}$—$COOR_{14}$, —$(CH_2)_{m1}$—$CONHR_{14}$, —$(CH_2)_{m1}$—CN, in which m1 has the meaning above, —$SO_2$—NH—$SO_2$—$R_{14}$, —NH—$SO_2$—$R_{14}$, —$PO_3R_{14}$, —NH—$SO_2$—$CF_3$, —$SO_2$—NH—$SO_2$—$R_{14}$, —NH—$SO_2$—$R_{14}$, —$PO_3R_{14}$, —NH—$SO_2$—$CF_3$ and

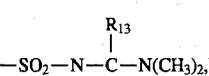

—$(CH_2)_{m1}$—$SO_3R_{14}$, —CO—NH—$OR_{14}$,
—CO—NH—NH—$SO_2$—$CF_3$, —CO—NH—$SO_2$—$R_{14}$,
—$CH_2SO_2NHCO$—$R_{14}$,
—$CH_2CONH$—$SO_2R_{14}$, —$NHSO_2NHCOR_{14}$, —NH-$CONHSO_2$—$R_{14}$,
—$CONHSO_2NR_{14}R_{15}$, —$SO_2NHCONR_{14}R_{15}$,
—$SO_2N(R_{14})OR_{15}$, —$SO_2NHPO(R_{14})_2$, —$CONHPO(R_{14})_2$, —$SO_2NHCN$, $SO_2NHCOR_{14}$, —$SO_2NHSO_2NR_{14}R_{15}$,
—$SO_2NHSO_2N(CH_2CH_2)_2Y$,
—$NHSO_2NHSO_2R_{14}$, —$NHSO_2NHPO(R_{14})_2$,
—$NR_{14}COCO_2H$,

—$SO_2NHCO_2R_{14}$, in which $R_{13}$ has the definition above and $R_{14}$ and $R_{15}$ are individually selected from the group consisting of hydrogen, alkyl of 1 to 6 carbon atoms, optionally substituted cycloalkyl of 3 to 6 carbon atoms, and Y is oxygen or sulfur, all the alkyl, alkenyl, cycloalkyl, alkylthio, phenylthio, alkoxy, phenyl, benzyl being optionally substituted by at least one member of the group consisting of halogen, hydroxyl, nitro, alkyl, alkenyl and alkoxy of up to 4 carbon atoms, trifluoromethyl, cyano, amino, mono and dialkylamino, free, salified or esterified carboxy, haloalkyl, alkylthio, haloalkylthio, haloalkoxy, phenyl, pyridyl, benzyl, phenethyl, benzoyl, phenoxy, benzyloxy, phenylthio, carbamoyl, acyl, acyloxy and tetrazolyl, the products of formula I being in all possible racemic, enantiomeric and diastereoismoeric isomer forms, as well as the addition salts with mineral and organic acids or with mineral and organic bases of the said products of formula comprises reacting a compound of the formula

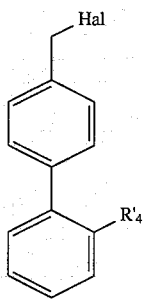

A wherein Hal is halogen and $R'_4$ has the meaning indicated above for $R_4$ in which the optional reactive functions are optionally protected with an oxidizing agent to obtain a compound of the formula

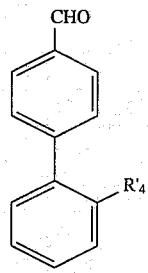

B in which $R'_4$ has the meaning above, reacting the latter with a compound of the formula

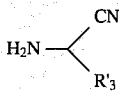

II in which $R'_3$ has the meaning indicated above for $R_3$ in which the optional reactive functions are optionally protected to obtain a product of the formula

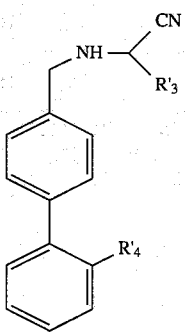

C in which $R'_3$ and $R'_4$ have the meanings above, reacting the latter with a compound of the formula

III in which $R'_1$ has the meaning indicated above for $R_1$ in which the optional reactive functions are optionally protected and Hal is halogen to obtain a product of the formula

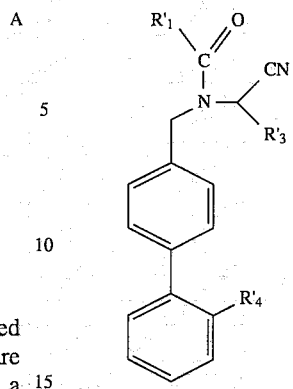

D in which $R'_1$ and $R'_3$ and $R'_4$ have the meanings above, subjecting the latter to an addition reaction on the CN with a reagent capable of introducing $R'_2$ having the meaning above for $R_2$ in which the optional reactive functions are optionally protected to obtain a product of the formula

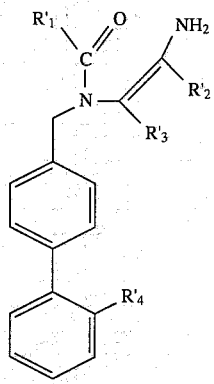

E in which $R'_1$, $R'_2$, $R'_3$ and $R'_4$ have the meanings above, optionally subjecting the latter to a substitution reaction of the oxygen by a sulfur to obtain a product of the formula

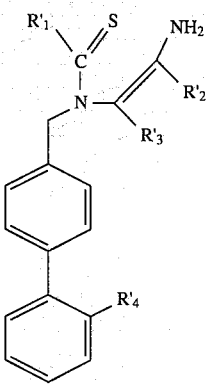

L in which $R'_1$, $R'_2$, $R'_3$ and $R'_4$ have the meanings above, subjecting the product of formula E or the product of formula L to a cyclization reaction to obtain a product of the formula

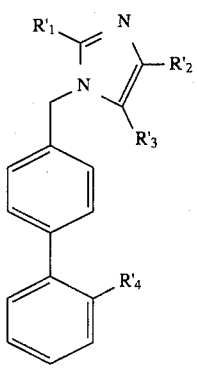

in which R'$_1$, R'$_2$, R'$_3$ and R'$_4$ have the meanings above, it being understood that the products of formulae E and L during the above process, and the products of formula I' can optionally be subjected to one or more of the following reactions in any order:
a) an esterification reaction of the acid function,
b) a saponification reaction of the ester function,
c) a conversion reaction of the cyano function into an acid function,
d) a reduction reaction of the carboxy function into an alcohol function,
e) a conversion reaction of the alkoxy function into a hydroxyl function,
f) an oxidation reaction of the group containing a sulfur atom into the corresponding sulfoxide or sulfone,
g) a conversion reaction of the alcohol or sulfone function into a corresponding aldehyde or acid function,
h) a conversion reaction of the nitrile radical into tetrazole,
i) a conversion reaction of the formyl into carbamoyl,
j) a conversion reaction of the carbamoyl into a nitrile,
k) a conversion reaction of

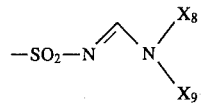

into

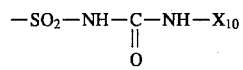

in which X$_8$, X$_9$ and X$_{10}$, individually are hydrogen or alkyl or alkenyl of up to 4 carbon atoms, optionally substituted, which products of formula I' can be products of formula I or which are optionally subjected to obtain the products of formula I to one or more of the following reactions in any order:
a) an elimination reaction of the protective groups that are carried by the protected reactive functions,
b) a salification reaction by a mineral or organic acid or by a base to obtain the corresponding salt,
c) a resolution reaction of the racemic forms into resolved products,
said products of formula I thus obtained being in all possible racemic, enantiomeric and diastereoisomeric isomer forms.

In —(CH$_2$)$_{m1}$—S(O)$_{m2}$—X—R$_{10}$, when m$_1$ is other than 0, —(CH$_2$)$_{m1}$— is alkylene such as methylene, ethylene, n-propylene or n-butylene and preferably when m is 0, 1 or 2, —(CH$_2$)$_{m1}$— is a single bond, methylene or ethylene. —S(O)$_{m2}$—X—R$_{10}$ moiety may be in a non-exhaustive manner selected from the group consisting of:
—SO$_2$—NH$_2$, —SO$_2$—NH—CH$_3$, —SO$_2$—NH—CF$_3$, —SO$_2$—NH—C$_6$H$_5$,
—SO$_2$—NH—CH$_2$—C$_6$H$_5$, —CH$_2$—SO$_2$—NH$_2$, —CH$_2$—SO$_2$—NH—C$_6$H$_5$,
—SO$_2$—NH—CO—NH—CH$_3$, —SO$_2$—NH—CO—NH—C$_6$H$_5$, —SO$_2$—NH—CO—NH—CF$_3$,
—SO$_2$—NH—CO—NH—CH$_2$—C$_6$H$_5$, —SO$_2$—NH—CO—NH—D in which D is phenyl, pyridine or pyrimidine

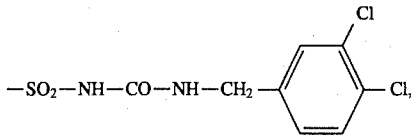

—SO$_2$—NH—CO—NH—CH$_2$—CH$_2$—CH$_3$,
—SO$_2$—NH—CO—NH—CH=CH—CH$_3$,

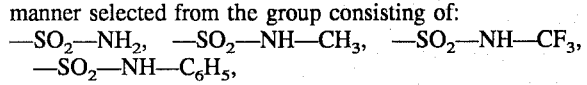

in which A and B are chosen from hydrogen, phenyl, pyridyl and pyrimidyl.

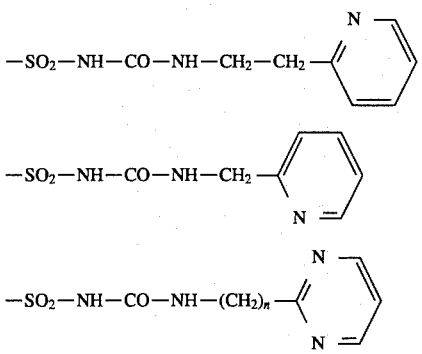

with n = 1 or 2.

In the products of formula I and in what follows: the alkyl preferably designates methyl, ethyl, propyl, isopropyl, butyl isobutyl, sec.-butyl and tert-butyl but can also be pentyl or hexyl and particularly isopentyl and isohexyl. The term alkenyl preferably designates vinyl, allyl, 1-propenyl, butenyl and particularly 1-butenyl or pentenyl. The term alkynyl preferably designates ethynyl, propynyl and linear or branched butynyl.

Among the alkyls interrupted by one or more heteroatoms, there are methoxymethyl, methoxyethoxymethyl, propylthiopropyl, propyloxypropyl, propylthioethyl, methylthiomethyl. Halogen preferably designates chlorine or bromine, but can also be fluorine or iodine. The term alkoxy preferably designates methoxy, ethoxy, propoxy or isopropoxy, but can also be n- or secondary or tertiary butoxy.

The acyl preferably is derived from an organic carboxylic acid of 1 to 6 carbon atoms such as formyl, acetyl, propionyl, butyryl or benzoyl, but also pentanoyl, hexanoyl, acryloyl, crotonoyl or carbamoyl. The amino substituted by one or two alkyls preferably designates groups in which the alkyl is chosen from the alkyls defined above such as for monoalkyl amino, methylamino or ethylamino, or for dialkylamino dimethylamino or methylethylamino. Acyloxy designates an acyl with the values indicated above may be formyloxy, acetyloxy, propionyloxy, butyryloxy or benzoyloxy. Cycloalkyl preferably designates cyclopropyl, cyclobutyl, cyclopentyl or cyclohexyl.

The monocyclic and condensed rings designate saturated or unsaturated rings. Examples of saturated monocyclic are pyrrolidinyl, imidazolidinyl, pyrazolidinyl, piperidyl, piperazinyl, morpholinyl, thio-morpholinyl, azepinyl, or unsaturated monocycles such as: pyrannyl, pyrrolyl, imidazolyl, pyrazolyl, pyridyl, pyrazinyl, pyrimidinyl, pyridazinyl, thiazolyl, thiadiazolyl, oxazolyl, furazannyl, pyrrolinyl such as delta 2-pyrrolinyl, imidazolinyl such as delta 2-imidazolinyl, pyrazolinyl such as delta 3-pyrazolinyl as well as the position isomers of the heteratom or heteroatoms which these radicals can contain such as isothiazolyl or isoxazolyl.

The condensed rings may be saturated such as 1-oxa spiro [4,5]decyl, tetrahydropyran-2-spirocyclohexyl, cyclohexanespiro-2'-(tetrahydrofuran) or 1, 10-diaza anthr-4-yl, or unsaturated such as benzothienyl, naphtho[2,3-b]thienyl, idenyl, indolizinyl, isoindolyl, 3H-indolyl, indolyl, indazolyl, purinyl, quinolizinyl, benzopyrrolyl, benzimidazolyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, indolinyl, isoindolinyl and also condensed polycyclic systems constituted by heterocyclic monocycles as defined above such as furo[2,3-b]pyrrole or thieno[2,3-b]furan.

Haloalkyl is the alkyl as defined above and is substituted by one or more halogens as defined above for example bromoethyl, trifluoromethyl, trifluoroethyl or pentafluoroethyl. Alkylthio preferably is the alkyl as defined above, for example methylthio or ethylthio and haloalkylthio preferably is the alkyl as defined above, for example methylthio or ethylthio and haloalkylthio preferably is the alkyl as defined above and is substituted by one or more halogens as defined above, for exampled bromoethylthio, trifluoromethylthio, trifluoroethylthio or pentafluoroethylthio. Haloalkoxy preferably is the alkoxy as defined above and is substituted by one or more halogens as defined above, for example bromoethoxy, trifluoromethoxy, trifluoroethoxy or pentafluoroethoxy.

Carbamoyl also designates carbamoyl substituted by a lower N-monoalkyl carbamoyl such as N-methylcarbamoyl, N-ethylcarbamoyl, a lower N,N-dialkyl carbamoyl such as N,N-dimethylcarbamoyl, N,N-diethylcarbamoyl; and N-(lower hydroxyalkyl) carbamoyl such as N-(hydroxymethyl) carbamoyl, N- (hydroxyethyl) carbamoyl, a lower carbamoylalkyl such as carbamoylmethyl and carbamoylethyl. Phenyl substituted by an alkylthio is for example benzylthio.

In the products of formula I and in what follows, the alkyl, alkenyl, cycloalkyl and phenyl which ca be represented by or carried by $R_1$, $R_2$ and $R_3$ can take the valuses defined above and may or more note substituted by one or more identical or differnet substituents as defined above. Therefore, $R_2$ and $R_3$ can, for example, be alkylthio, phenylthio, alkylsulfine phenylsulfinyl, alkylsufonyl or arylsufonyl but also cycloalkylthio such as cyclohexylthio: Alkylthio, alkylsulfuinyl and alkylsufonyl may be linear or branched alkyl as indicated above the the alkyl. Examples are, methylthio, hydroxymethylthio, ethylthio, aminoethylthio, methylsulfinyl, ethylsulfinyl, methylsulfonyl, ethylsulfonyl, propylthio, isopropylthio, butylthio, sec-butylthio, ter-butylthio, isopentylthio or isohexylthio or those in which the thio is oxidized into the sulfinyl or sulfonyl.

Depending to the values of m1, m2 and $R_{10}$ in $-(CH_2)_{m1}-S(O)_{m2}-X-R_{10}$, $R_2$ and $R_3$ can also be phenylthio, pyridylthio or pyrimidylthio, imidazolylthio, N-methylimidazolylthio as well as those in which the thio is oxidized into the sulfinyl or sulfonyl such as phenylsulfinyl or phenylsulfonyl.

As examples of substituted alkyls, there are those substituted by one or more phenyl for example, benzyl, diphenylmethyl and tripehnylmethyl, and those substituted by pyridyl, for example pyridylmethyl, it being understood that in the non-exhaustive list of examples as mentioned above, the alkyl can also just as equally be ethyl, propyl or butyl such as phenylethyl.

Examples of substituted alkenyl are those substituted with at least one phenyl or pyridyl, as indicated in the examples given above in which the alkyl is replaced by an alkenyl for example phenylvinyl or phenylallyl.

The carbamoyl and amino radicals mentioned above in particular:

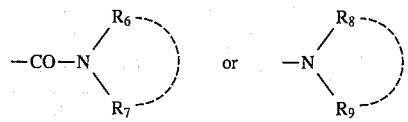

designate groups in which two identical or different groups are linked to the nitrogen atom selected from the group consisting of hydrogen to obtain the amino; the alkyl as defined above to obtain the monoalkyl- or dialkylamino in which the linear or branched alkyl have 1 to 6 carbon atoms and particularly methyl, ethyl, isopropyl, methoxymethyl, methoxyethyl, ethoxyethyl radicals; the phenyl, benzyl, phenethyl optionally substituted to obtain the phenylamino or benzylamino.

Among the substituted carbamoyl, there are lower N-monoalkyl carbamoyl, for example, N-methylcarbamoyl, N-ethylcarbamoyl; the lower N,N-dialkyl carbamoyl, for example, N,N-dimethylcarbamoyl, N,N-diethylcarbamoyl; the N-(lower hydroxyalkyl) carbamoyl, for example, N-(hydroxymethyl) carbamoyl, N-(hydroxyethyl) carbamoyl; the lower carbamoylalkyl, for example carbamoylmethyl, carbamoylethyl; phenylcarbamoyl; pyridylcarbamoyl; benzylcarbamoyl; N-methyl N-phenylcarbamoyl; pyridylmethylcarbamoyl.

The expression amino acid preferably designates a remainder derived from one of the natural amino acids such as glycine, alanine, valine, leucine, isoleucine, phenylalanine and particularly proline or one of the other natural amino acids known to one skilled in the art.

Among the $-(CH_2)_{m1}-X-R_{10}$ which can be represented by $R_6$, $R_7$, $R_8$ or $R_9$ are $-NH-SO_2-CH_3$, $-NH-SO_2-C_6H_5$, $-NH-SO_2-CF_3$, $-NH-CH_2-SO_2-NH-C_6H_5$, $-CO-NH-SO_2-C_2H_5$, $-CO-NH-SO_2-CH_3$, $-CO-NH-SO_2$ $-CH_2-C_6H_5$. The heterocycle which can be formed with $R_6$ and $R_7$ or $R_8$ and $R_9$ is preferably saturated.

It can be optionally substituted by the substituents already mentioned previously and particularly by one or more members selected from the group consisting of chlorine and fluorine, methyl, ethyl, isopropyl, tert-butyl, methoxy, ethoxy, propoxy, benzoyl, methoxycarbonyl, ethoxycarbonyl, for example methylpiperazinyl, ethylpiperazinyl, propylpiperazinyl, phenylpiperazinyl or benzylpiperazinyl. In these last two, the phenyl and benzyl can be substituted as indicated previously for example chlorophenyl or trifluorophenyl.

The acyl of $R_8$ and $R_9$ can be chosen from acetyl, propionyl, butyryl, pentanoyl and carbamoyl. When $R_8$ or $R_9$ is alkoxy-carbonyl, this is preferably tert-butyloxycarbonyl.

The carboxy of the products of formula I can be salified or esterified by various groups known to one skilled in the art among which there can be mentioned, for example: among the salification compounds, mineral bases such as sodium, potassium, lithium, calcium, magnesium or ammonium salt or organic bases such as methylamine, propylamine, trimethylamine, diethylamine, triethylamine, N,N-dimethylthanolamine, tris (hydroxymethyl) amino methane, ethanolamine, pyridine, picoline, dicyclo-hexylamine, morpholine, benzylamine, procaine, lysine, arginine, histidine, N-methylglucamine.

Among the esterification compounds are alkyl to form alkoxy carbonyl groups such as methoxycarbonyl, ethoxycarbonyl, tertbutoxycarbonyl or benzyloxycarbonyl which alkyls may be substituted by members selected from the group consisting of halogen, hydroxyl, alkoxy, acyl, acyloxy, alkylthio, amino or aryl such as chloromethyl, hydroxypropyl, methoxymethyl, propionyloxymethyl, methylthiomethyl, dimethylaminoethyl, benzyl or phenethyl.

The addition salts with mineral or organic acids of the products of formula I can be the salts formed with the following acids: hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid, alkylmonosulphonic acid such as methanesulfonic acid, ethanesulfonic acid, propanesulfonic acid, alkyldisulfonic acid such as methanedisulfonic acid, α,β-ethanedisulfonic, arylmonosulfonic such as benzenesulfonic acid and aryldisulfonic acid.

When $R_2$ and $R_3$ both are individually an optionally oxidized sulfurous alkylthio or phenylthio, the preferred products of the invention are particularly the products of formula I in which these sulfurous groups have the same degree of oxidation.

Among the preferred compounds of formula I are those wherein one of $R_2$ and $R_3$ is an optionally oxidized sulfur group as defined above and the other is alkyl, alkoxy, free, salified or esterifed carboxy or optionally substituted phenyl, preferably $R_2$ is the sulfurous group. $R_2$ and/or $R_3$ may be alkylthio or alkenylthio optinally substituted with at least one member of the group consisting of formyl, —OH, alkoxy, acyloxy, free, salified or esterified carboxy; amino; substituted amino; carbamoyl; substituted carbamoyl; alkylthio; phenylthio; pyridinyl; pyrimidinyl; phenyl.

Among the substituents which can be carried by $R_2$ and $R_3$ are amino and carbamoyl, particularly substituted by one or two alkyl and amino acids mentioned above. The substituted amino and carbamoyl which can be carried by $R_2$ and $R_3$ can also form a heterocycle such as those mentioned above.

Also $R_2$ and $R_3$ can be alkylthio substituted by one or more halogens such as chlorine and fluorine such as —S—CF$_3$; —S—CHF$_2$; —S—CH$_2$F; —S—CF$_2$—CHF$_2$; —S—CF$_2$—CHFCl.

$R_2$ and $R_3$ can represent the following in which n, n1 and n2, individually may be 0 to 2 such as

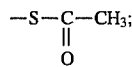

—SO$_3$H; —S—CH$_3$;
—S—(CH$_2$)$_{n1}$—S—(CH$_2$)$_{n2}$—X$_4$;
—S—(CH$_2$)$_n$—X$_4$;
—S—(CH$_2$)$_{n1}$—NH—(CH$_2$)$_{n2}$—X$_4$;
—S—(CH=CH—(CH$_2$)$_n$—X$_4$;
—S—(CH$_2$)$_{n1}$—CH=CH—(CH$_2$)$_{n2}$—X$_4$;
in which X$_4$ is H, OH, cyclohexyl, pyridyl, phenyl, CHO, COOH, NH$_2$ or

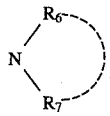

$R_2$ and $R_3$ can be particularly, —COOH; —CO$_2$X$_5$; —SX$_5$; —NH$_2$; —C≡N; —OMe; —OEt; —C=CH—COOH; tetrazolyl;

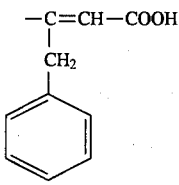

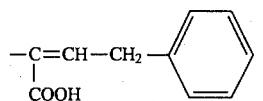

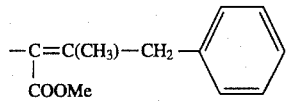

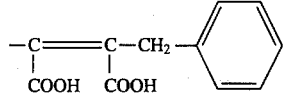

in all their isomer, cis-trans isomer forms,

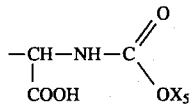

—NH—CH$_2$—COO—X$_5$
—NH—COO—X$_5$
X$_5$ is alkyl or aryl.

$R_2$ and $R_3$ can preferably be

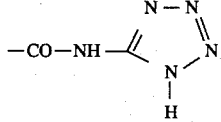

The products of formula I represent in particular products in which $R_2$ and $R_3$ have the meanings indicated above and quite particularly products in which $R_2$ is an optionally substituted alkylthio as defined above or an alkoxy such as methoxy and $R_3$ is a free, salified or esterified carboxy or an amidified carboxy such as —COOH, —COO-methyl, —COO-ethyl, —CONH$_2$ or

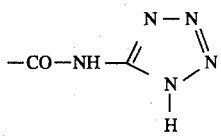

Among the preferred values of $R_4$ are cyano, —(CH$_2$)$_{m1}$—SO$_2$—X—R$_{10}$ as defined above and more particularly
—SO$_2$—NH—CO—NH—CH$_2$—CH=CH$_2$, —SO$_2$—NH—CO—NH—CH$_{2-CH2-CH3}$,
—SO$_2$—N$^-$—CO—NH—CH$_2$—CH$_2$—CH$_3$

K+

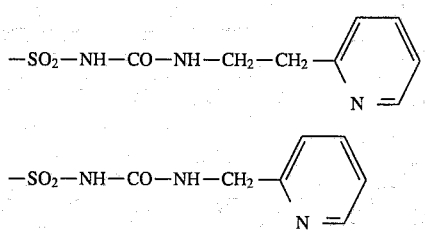

The invention is preferably the above process for the preparation of products of the formula

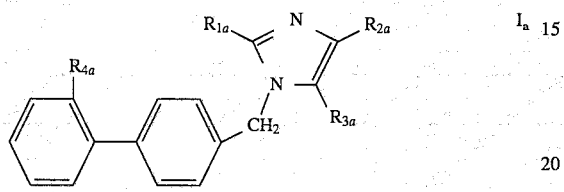

in which:
$R_{1a}$ is alkyl or alkenyl of up to 4 carbon atoms,
$R_{2a}$ and $R_{3a}$, are individually chosen from:
a) hydrogen, mercapto; formyl; free, salified or esterified carboxy; halogen; hydroxyl; cyano; nitro; acyl;
b) alkyl, alkenyl, alkoxy, alkylthio in which the sulfur atom is optionally mono- or dioxidized having up to 6 carbon atoms, phenyl, benzoyl, phenylthio in which the sulfur atom is optionally mono- or dioxidized, all being optionally substituted by at least one member of the group consisting of halogen, hydroxyl, trifluoromethyl, cyano, nitro, formyl, alkyl and alkoxy of 1 to 4 carbon atoms, phenyl and free, salified or esterified carboxy,
c)

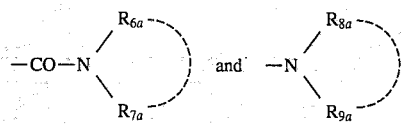

in which:
either $R_{6a}$, $R_{7a}$, $R_{8a}$ and $R_{9a}$ are individually chosen from hydrogen, amino acids, alkyl of 1 to 6 carbon atoms, phenyl, benzyl, phenethyl or $R_{6a}$ and $R_{7a}$ and $R_{8a}$ and $R_{9a}$ form respectively with the nitrogen atom to which they are linked a heterocyclic selected from the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepine, indolyl, optionally substituted by at least one member of the group consisting of halogen, hydroxyl, nitro, alkyl and alkoxy of 1 to 6 carbon atoms and phenyl, $R_{4a}$ is cyano, free, salified or esterified carboxy, $-(CH_2)_p-SO_2-X_a-R_{10a}$ in which p is 0 or 1, $X_a$ is $-NH-$, $-NH-CO-$, $-NH-CO-O-$, $-N=CH-N-R_{13a}$, $-NH-CO-NH-$ or a single bond and $R_{10a}$ and $R_{13a}$ are individually selected from the group consisting of alkyl or alkenyl of up to 6 carbon atoms and optionally substituted, pyridyl, phenyl, benzyl, nitropyridyl, pyrimidyl, tetrazolyl, diazolyl, piperidinyl, alkylpiperidinyl, thiazolyl, alkylthiazolyl, tetrahydrofuranyl and methyltetrahydrofuranyl;
the alkyl and alkenyl being optionally substituted by at least one member of the group consisting of halogen, hydroxyl, nitro, alkyl, alkenyl and alkoxy of up to 4 carbon atoms, trifluoro-methyl, cyano, amino, mono- and dialkylamino, free, salified or esterified, carboxy, phenyl and tetrazolyl;
the said products of formula $I_a$ being in all possible racemic, enantiomeric and diastereoisomeric isomer forms, as well as the addition salts with mineral and organic acids or with mineral and organic bases of the said products of formula $I_a$, characterized in that for their preparation as defined above, products of formulae A, II, III and a reagent capable of introducing the $R'_2$ are used in which $R'_1$, $R'_2$, $R'_3$ and $R'_4$ have the values indicated above for $R_{1a}$, $R_{2a}$, $R_{3a}$ and $R_{4a}$ respectively in which the reactive functions are optionally protected.

Another preferred process of the invention of the process for the preparation of compounds of the formula

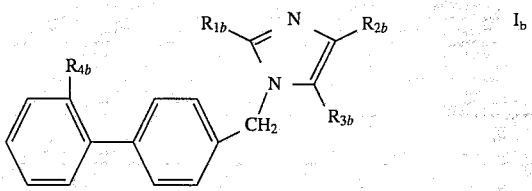

in which:
$R_{1b}$ is alkyl of up to 1 to 4 carbon atoms, $R_{3b}$ is hydrogen, formyl, acyloxy, alkyl or alkoxy optionally substituted or carboxy free, salified or esterified by an alkyl, $R_{2b}$ is optionally substituted phenylthio, phenylsulfonyl, phenylsulfinyl, alkylthio, alkylsulfonyl or alkylsulfinyl such as in all those represented by $R_{2b}$ and $R_{3b}$, alkyl and alkoxy of 1 to 6 carbon atoms, and the phenyl is optionally substituted by one or more groups chosen from halogen, hydroxyl, trifluoromethyl, acyloxy, free, salified or esterified carboxy, phenyl, pyridyl, tetrazolyl, alkyl and alkoxy of 1 to 4 carbon atoms optionally substituted by alkoxy of 1 to 4 carbon atoms, $R_{4b}$ is cyano, free, salified or esterified carboxy, $-SO_2-X_b-R_{10b}$ radical in which $X_b$ is $-NH-$, $-NH-CO-$, $-NH-CO-O-$, $-N=CH-N-R_{13b}$, $-NH-CO-NH-$ or a single bond and $R_{10b}$ and $R_{13b}$ are, individually selected from the group consisting of hydrogen, methyl, ethyl, propyl, vinyl, allyl, pyridyl, phenyl, benzyl, nitropyridyl, pyrimidyl, tetrazolyl, diazolyl, piperidinyl, alkylpiperidinyl, thiazolyl, alkyl-thiazolyl, tetrahydrofuranyl and methyltetrahydrofuranyl, the said products of formula $I_b$ being in all possible racemic, enantiomeric and diastereoisomeric isomer forms, as well as the addition salts with mineral and organic acids or with mineral and organic bases of said products of formula $I_b$, characterized in that for their preparation as defined above, products of formulae A, II, III and a reagent capable of introducing $R'_2$ are used in which $R'_1$, $R'_2$, $R'_3$ and $R'_4$ have the values indicated above for $R_{1b}$, $R_{2b}$, $R_{3b}$ and $R_{4b}$ respectively in which the reactive functions are optionally protected.

A more particular subject of the invention is the process for the preparation of products of the formula

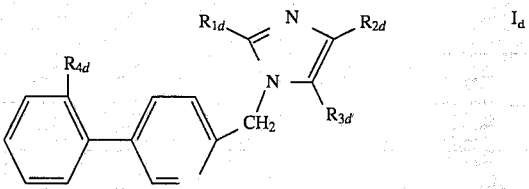

in which:
$R_{1d}$ is alkyl of 1 to 4 carbon atoms, $R_{3d}$ is selected from the group consisting of carboxy free, salified or esterified by alkyl of 1 to 4 carbon atoms, formyl, acyloxy, alkyl of 1 to 4 carbon atoms optionally substituted by hydroxyl, $R_{2d}$ is selected from the group consisting of phenylthio, phenylsulfonyl, phenylsulfinyl, alkylthio, alkylsulfonyl or alkylsulfinyl in which the alkyl has 1 to 4 carbon atoms, and $R_{4d}$ is —SO$_2$—NH$_2$, —SO$_2$—NH—CO—O—$R_{10d}$, —SO$_2$—N=CH—NR$_{13d}$, or —SO$_2$—NH—CO—NH—$R_{10d}$ in which $R_{10d}$ and $R_{13d}$ are individually selected from the group consisting of hydrogen, methyl, ethyl, n-propyl and propenyl, the said products of formula $I_d$ being in all possible racemic, enantiomeric and diastereoisomeric isomer forms, as well as the addition salts with mineral and organic acids or with mineral and organic bases of said products of formula $I_d$, characterized in that for their preparation as defined above, products of formulae A, II and III and a reagent capable of introducing $R'_2$ are used in which $R'_1$, $R'_2$, $R'_3$ and $R'_4$ have the values indicated above for $R_{1d}$, $R_{2d}$, $R_{3d}$ and $R_{4d}$ respectively in which the reactive functions are optionally protected.

A particular subject of the invention is the process as defined above, characterized in that a product of formula A is used in which $R'_4$ is —SO$_2$—NH$_2$, —SO$_2$—NH—CO—O—$R_{10d}$, —SO$_2$—N=CH—NR$_{13d}$, or —SO$_2$—NH—CO—NH—$R_{10d}$ in which $R_{10d}$ and $R_{13d}$, are individually chosen from hydrogen, methyl, ethyl, n-propyl and propenyl, in which the reactive functions are optionally protected, a product of formula II in which $R'_3$ is carboxy free salified or esterified by alkyl of 1 to 4 carbon atoms, formyl, acyloxy, or alkyl of 1 to 4 carbon atoms optionally substituted by a hydroxyl, a product of formula III in which $R'_1$ is alkyl of 1 to 4 carbon atoms, and a reagent capable of introducing $R'_2$ in which $R'_2$ represents phenylthio, phenylsulfonyl, phenylsulfinyl, alkylthio, alkylsulfonyl or alkylsulfinyl, in which the alkyl has 1 to 4 carbon atoms, and the reactive functions are optionally protected.

A more preferred subject of the invention is the process as defined above, in which the product of formula A is used in which $R'_4$ is

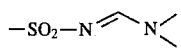

a product of formula II is used in which $R'_3$ is free salified or esterified alkoxy carboxy, a product of formula III is used in which $R'_1$ is alkyl of 1 to 4 carbon atoms and a reagent capable of introducing $R'_2$ when $R'_2$ is alkylthio or phenylthio optionally oxidized in the form of the sulfoxide or sulfone, the alkoxy, alkylthio and phenylthio being optionally substituted by one or more groups chosen from halogen, alkyl or alkoxy of 1 to 4 carbon atoms, trifluoromethyl, amino, mono or dialkylamino, cyano, phenyl, hydroxyl, free, salified or esterified carboxy, acyl and acyloxy.

Therefore, the process as defined above is characterized in that a compound of the formula

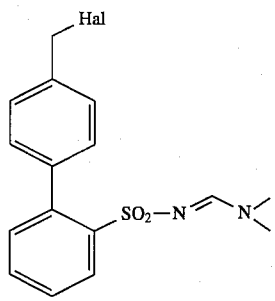

A$_1$ in which Hal is halogen reacted with an oxidizing agent to obtain a compound of the formula

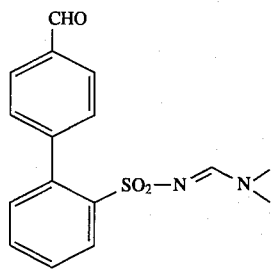

B$_1$ which is reacted with a compound of the formula

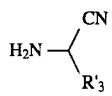

II in which $R'_3$ has the meaning indicated above to obtain a product of the formula

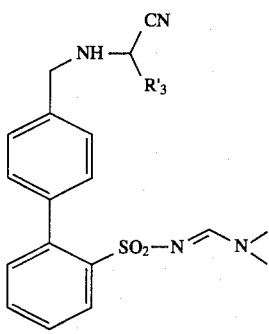

C$_1$ in which $R'_3$ has the meaning indicated above which is reacted with a compound of the formula $R'_1$—CO—Hal                                III in which $R'_1$ and Hal have the meaning above to obtain a product of the formula

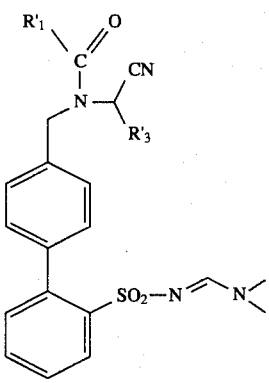

D$_1$ in which $R'_1$ and $R'_3$ have the meanings above, which either is subjected to an addition reaction on the CN, using a reagent capable of introducing $R'_2$ as defined above to obtain the product of the formula

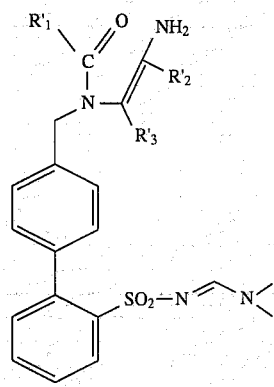

in which R'₁, R'₂ and R'₃ have the meanings above which is optionally subjected to a substitution reaction of the oxygen of by a sulfur to obtain a product of the formula

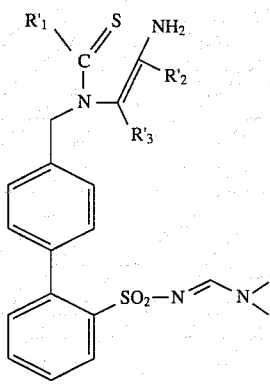

in which R'₁, R'₂ and R'₃ have the meanings above, which optionally is converted into the a product of the formula

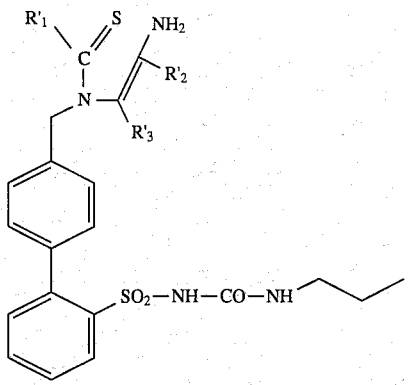

in which R'₁, R'₂ and R'₃ have the meanings indicated above, which product of formula E₁, L₁ or L₂ is subjected to a cyclization reaction in order to obtain a product of the formula

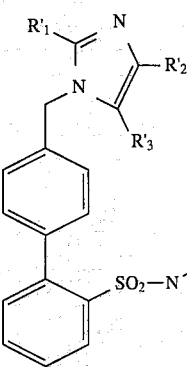

or

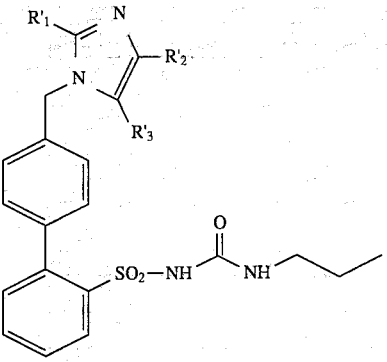

in which R'₁, R'₂ and R'₃ have the meanings above and optionally the product of formula I'₁ is converted into the product of formula I'₂ as defined above or the product of formula D₁ is subjected to an addition reaction on the

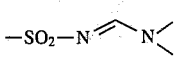

to obtain a product of the formula

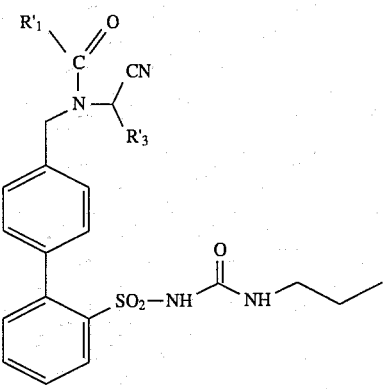

in which R'₁ and R'₃ have the meanings above, which is subjected to an addition reaction on the CN as indicated above to obtain a product of the formula

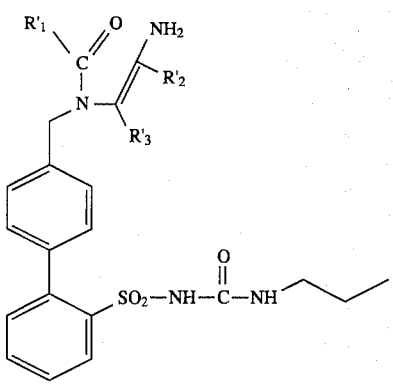

in which R'₁, R'₂ and R'₃ have the meanings above, which is subjected to a cyclization reaction to obtain a product of formula I'₂ as defined above.

A particular subject of the invention is the process as defined above for the preparation of products of formula I corresponding to 2-butyl-1-[[2'-carboxy-(1,1'-biphenyl)-4-yl]methyl]-4-(phenylthio)-1H-imidazole-5-carboxylic acid
-2-butyl-1-[[2'-carboxy-(1,1'-biphenyl)-4-yl]-methyl]-4
   -(methylthio)-1H-imidazole-5-carboxylic acid,
-4'-[[2-butyl-4-(ethylthio)-5-(hydroxymethyl)-1H-imidazol-
   1-yl]methyl]-(1,1'-biphenyl)-2-carboxylic acid,
-2-butyl-1-[[2'-carboxy-(1,1'-biphenyl)-4-yl]-methyl]-4
   -(ethylsulfonyl)-1H-imidazole-5-carboxylic acid,
-2-butyl-1-[[2'-carboxy-(1,1'-biphenyl)-4-yl]-methyl]-4
   -(ethylsulfinyl)-1H-imidazole-5-carboxylic acid,
-2-butyl-1-[[2'-carboxy-(1,1'-biphenyl)-4-yl]-methyl]-4
   -(ethylthio)-1H-imidazole-5-carboxylic acid,
-2-butyl-1-[[2'-carboxy-(1,1'-biphenyl)-4-yl]-methyl]-4
   -(phenylsulfonyl)-1H-imidazole-5-carboxylic acid,
-2-butyl-1-[[2'-carboxy-(1,1'-biphenyl)-4-yl]-methyl]-4
   -(phenylsulfinyl)-1H-imidazole-5-carboxylic acid,
-2-butyl-1-[[2'-tetrazolyl-(1,1'-biphenyl)-4-yl]-methyl]-4
   -(methylthio)-1H-imidazole-5-carboxylic acid, A more particular subject of the invention is the process as defined above for the preparation of products of formula I corresponding to-ethyl 2-butyl-4-(methyl-thio)-1-[[2'-((((propylamino)-carbonyl)-amino)-sulfonyl)-(1,1'-biphenyl)-4-yl]-methyl]-1H-imidazole-5-carboxylate,
-2-butyl-4-(methylthio)-1-[[2'-((((propylamino)-carbonyl)-amino)-sulfonyl)-(1,1'-biphenyl)-4-yl]-methyl]-1H-imidazole-5-carboxylic acid and
-2-butyl-4-(methylthio)-1-[[2'-((((propylamino)-carbonyl)-amino)-sulfonyl)-(1,1'-biphenyl)-4-yl]-methyl]-1H-imidazole-5-carboxylic acid,-di-potassium-salt.

In the preferred conditions for the process of the invention, the product of formula B can be obtained by oxidation of the halide of formula A by means of hexamethylenetetramine in 50% acetic acid or N-oxide-N-methyl morpholine in a solvent such as dichloromethane, dichloroethane or toluene. The product of formula A is such that Hal is preferably bromine but can also be chlorine or iodine.

The reaction of the compound of formula B with the compound of formula II can be carried out by a reducing amination, brought about in two stages: The first stage is the formation of the imine of the product of formula B by the addition of the product of formula II on the aldehyde function of the product of formula B, in a solvent such as dichloromethane, dichloroethane or tetrahydrofuran preferably under acid catalysis conditions, for example in the presence of amberlyst H⁺ or also acetic acid. The second stage is the reduction of the imine formed by a reducing agent such as $NaBH_3CN$ or $NaBH(OAc)_3$ (prepared previously from sodium borohydride and acetic acid).

The product of formula C is converted into the product of formula D by an acylation agent, for example an acid halide such as butyryl or valeryl chloride in the presence of sodium or potassium carbonate, pyridine or triethylamine in a solvent such as acetone, tetrahydrofuran, dichloromethane or dichloroethane.

The product of formula D is converted into the product of formula E by the addition of R'₂ on the cyano function which amidification can take place in a solvent such as an alcohol like methanol or ethanol, by reaction of R'₂—SH on the cyano function in a solvent such as toluene, tetrahydrofuran or dichloroethane.

In the case where R'₂ contains a sulfur, the reaction of the product of formula D to obtain the corresponding product of formula E is a thioamidification carried out by the action of a compound of formula R₁₀—SH in which R₁₀ is the remainder of the R'₂ as defined above and notably alkyl of 1 to 4 carbon atoms or phenyl optionally substituted as indicated above.

The thioamidification can be carried out by bubbling the compound of formula R₁₀—SH as defined above in a solvent such as an alcohol like ethanol or methanol or dichloroethane, dichloromethane, toluene, tetrahydrofuran in the presence of a base like triethylamine. The thioamidification can also be carried out with the R₁₀SNa or R₁₀SK reagent under the same solvent conditions defined for R₁₀SH.

The substitution reaction of the oxygen by a sulfur to obtain the product of formula L can be carried out with Lawesson reagent. The cyclization reaction of the product of formula E into the product of formula I' can be carried out either by an acid catalysis using amberlyst H⁺, tosylic acid or sulfuric acid in a solvent such as toluene, ethyl acetate, dichloromethane, dichloroethane, or with pentachloride in pyridine or dimethylaminopyridine, or also in dimethylsulfone.

The various reactive functions that can be carried by certain compounds of the reactions defined above can, if necessary, be protected. They can be for example hydroxyl, acyl, free carboxy or also amino and monoalkylamino which can be protected by appropriate protective groups. A list of the different protective groups which can be used will be found for example in the French Patent No. 2,499,995.

The following non-exhaustive list of examples of the protection of the reactive functions can be mentioned:
—the hydroxyl groups can be protected for example by alkyl such as tert-butyl, trimethylsilyl, tert-butyldimethylsilyl, methoxymethyl, tetrahydropyrannyl, benzyl or acetyl. The amino groups can be protected for example by acetyl, trityl, benzyl, tertbutoxycarbonyl, phthalimido or by others known in the chemistry of the peptides. Acyl groups such as formyl can be protected in the form of cyclic or non-cyclic ketals such as dimethyl- or diethylketal or ethylene dioxyketal and the acid functions of the products can be optionally amidified by a primary or secondary amine for example in methylene chloride in the presence of 1-ethyl-3-(dimethylaminopropyl)-carbodiimide hydrochloride at ambient temperature. The acid functions can be protected for example in the form of esters formed with easily-cleavable esters such as benzyl or ter-butyl esters or esters known in the chemistry of the peptides.

As for the products of formula I', the products of formulae D and E can be subjected during the process described above to the various reactions indicated above and notably reactions relating to R'₄ as defined above Thus, the product of formula E₁ can be converted into product E₂ before continuing the synthesis as indicated above for the conversion of product D₁ into product D₂.

Depending upon the values of $R'_1$, $R'_2$, and $R'_3$ and $R'_4$, the products of formulae I', $I'_1$ or $I'_2$ as defined above constitute or do not constitute products of formula I.

The reactions to which the products of formulae D, E and I' as defined above can be optionally subjected, can be carried out, for example, as indicated below.

a) The products described above can optionally be subjected to on the optional carboxy functions, a salification reaction by a mineral or organic base or an esterification reaction. These esterification and salification reactions can be carried out by the usual methods known to one skilled in the art.

b) The optional conversions of ester functions into an acid function can optionally be carried out under the usual conditions known to one skilled in the art, notably by alkaline or acid hydrolysis for example with sodium hydroxide or potassium hydroxide in an alcoholic medium such as in methanol or with hydrochloric or sulfuric acid.

c) The optional cyano functions of the products can optionally be converted into an acid function under the usual conditions known to one skilled in the art, for example by a double hydrolysis carried out in an acid medium such as in a mixture of sulfuric acid, glacial acetic acid and water, these three compounds being preferably in equal proportions, or in a mixture of sodium hydroxide, ethanol and water at reflux.

d) The optional free or esterified carboxy functions of the products above can optionally be reduced into an alcohol function by methods known to one skilled in the art. For the esterified carboxy functions, lithium aluminum hydride can be used in a solvent such as tetrahydrofuran or dioxane or ethyl ether. For the free carboxy functions, boron hydride can preferred be used.

e) The optional alkoxy functions such as methoxy of the products can optionally be, converted into a hydroxyl function under the usual conditions known to one skilled in the art, for example by boron tribromide in a solvent such as methylene chloride, by pyridine hydrobromide or hydrochloride or by hydrobromic or hydrochloric acid in water or by acetic acid at reflux.

f) The optional groups containing a sulfur atom of the products can optionally be converted into a corresponding sulfoxide or sulfone function under the usual conditions known to one skilled in the art, such as by means of a peracid such as peracetic acid or metachloroperbenzoic acid or by ozone, oxone, sodium periodate in a solvent such as methylene chloride or dioxane at ambient temperature.

The sulfoxide function can be obtained by an equimolar mixture of the product containing an alkylthio or arylthio group and a reagent such as a peracid. The sulfone function can be obtained by a mixture of the product containing an alkylthio or arylthio group with an excess of reagent such as a peracid.

g) The optional alcohol function of the products can optionally be converted into an aldehyde or acid function by oxidation under the usual conditions known to one skilled in the art such as by the action of manganese oxide to obtain the aldehydes or of Jones reagent to obtain the acids.

h) The optional nitrile functions of the products can optionally be converted into tetrazole under the usual conditions known to one skilled in the art, such as by cycloaddition of a metal azide such as a trialkyltin azide on the nitrile function as indicated in the method described in the article, KOZIMA et al, J. Organometallic Chemistry, Vol. 33, p. 337 (1971).

i) The conversion reactions of the formyl into a carbamoyl and of the carbamoyl into a nitrile are carried out according to the usual conditions known to one skilled in the art.

The products of formula I' are in addition optionally subjected to the reactions indicated below. The elimination of the protective groups under the usual conditions known to one skilled in the art, notably by an acid hydrolysis carried out with an acid such as hydrochloric, benzene sulfonic or p-toluene sulfonic acid, formic acid or trifluoroacetic acid or also by a catalytic hydrogenation. The phthalimido group can be eliminated by hydrazine.

The salification is carried out by a mineral or organic acid according to the usual methods known to one skilled in the art. The resolution of the racemics to obtain the optically active forms of the products of formula I is carried out by the usual methods known to one skilled in the art.

The products of formula I are known and described in European Patent Applications No. 0,465,368 and No. 0,503,162.

The products of formula I prepared according to the process as defined above as well as their addition salts with acids, have useful pharmacological properties. The products are endowed with antagonistic properties for the angiotensin II receptor and are inhibitors of the effects of angiotensin II, especially of the vasoconstrictive effect and also of the trophic effect at the level of the myocytes.

These properties justify the use in therapeutics of the products of formula I prepared by the process as defined above as medicaments, the said products of formula I being in all the possible racemic or optically active isomer forms, as well as the addition salts with pharmaceutically acceptable mineral or organic acids of said products of formula I. The products of formula I as well as their addition salts with pharmaceutically acceptable mineral or organic acids, can be used particularly as medicaments in the treatment of arterial hypertension, cardiac insufficiencies, renal insufficiencies and in the prevention of post-angioplastic recurrence of stenoses. They can also be used in the treatment of certain gastro-intestinal, gynaecological disorders and especially for a relaxing effect at the level of the uterus, in the form of pharmaceutical compositions containing as active ingredient at least one of the medicaments as defined above.

The pharmaceutical compositions can be administered buccally, rectally, parenterally or locally as a topical application on the skin and mucous membranes.

These compositions can be solid or liquid and can be presented in all the pharmaceutical forms currently used in human medicine such as tablets, dragees, capsules, granules, suppositories, injectable preparations, ointments, creams, gels and aerosol preparations by the usual methods. The active ingredient can be incorporated with the excipients usually employed in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according to the product used, the patient being treated and the illness in question, can be, for example, from 1 to 100 mg per day in an adult, by oral route.

Some of the starting products of formula A are known and can be prepared as indicated in the European Patent No. 0,503,162. The products of formula II are commercially-available products or can be prepared as indicated in the European Patent Application No. 0,465,368.

The products of formula III are commercially-available products or can be easily prepared from the acid or an appropriate derivative.

Also an object of the invention are the new industrial products, namely the compounds of formulae B, C, D, $D_1$, $D_2$, E, $E_1$, $E_2$, L, $L_1$ and $L_2$.

In the following examples, there are described several preferred embodiments to illustrate the invention. However, it is to be understood that the invention is not intended to be limited to the specific embodiments.

EXAMPLE 1:
2-butyl-4-(methylthio)-1-[[2'-[((propylamino) carbonyl)-amino)-sulfonyl]-1,1'(biphenyl)-4-yl]-methyl]-1H-imidazole-5 -carboxylic-acid di-potassium salt

STAGE A:
N-[(dimethylamino)-methylene]-4'-formyl-(1,1'-biphenyl)-2-sulfonamide 10 g of N-[(dimethylamino) methylene]4'-bromomethyl(1,1'-biphenyl)2-sulfonamide, 8.14 g of hexamethylene-tetramine and 80 ml of 50% acetic acid are were stirred for one hour at 120° C. and after the addition of 220 ml of water, the reaction mixture was neutralized with a saturated solution of sodium bicarbonate and extracted with dichloromethane. The extracts were dried and evaporated to obtain 7.99 g of the expected product.
MS MH⁺ 317 NMR (CDCl₃) 2.71 and 2.77

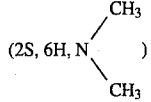

7.17 (s, N=CH—N) 7.15 to 7.91 (AB system, 6H, aromatics) 10.11 (CHO, 1H)

STAGE B: ethyl mono (4-methylbenzenesulfonate) aminocyano-acetate 50 g of ethyl (E) cyano(hydroxyimino) acetate were introduced into 440 ml of water and 340 ml of a sodium bi-sulfate solution, 150 g of sodium hydrosulfite were added and the mixture was stirred at about 35° C. for about 30 minutes. The solution was saturated by the addition of sodium chloride, extracted with methylene chloride and dried. The residue was taken up in ether and 44 g of p-toluene sulfonic acid in 110 ml of ethanol and 740 ml of ether were added. The solvents were eliminated to obtain 35 g of the expected product melting at 128°–130° C.

STAGE C: ethyl cyano-[[[2'-[[[(dimethylamino)methylene]amino] sulfonyl](1,1'-biphenyl)4-yl]methyl]amino]acetate A solution of 13 g of the product of Stage B, 1 g of amberlyst 15⁻(H⁺) and 12.3 g of the product of Stage A in dichloromethane was stirred at reflux for about 7 hours. The solution was cooled, then added to a suspension of 3.1 g of sodium borohydride, 14.2 ml of glacial acetic acid and 60 ml of dichloromethane at 10° C. The solution was stirred for about 18 hours. 200 ml of water were added and the precipitate obtained was filtered. The organic phase was washed with water, dried and concentrated under vacuum. After purification by chromatography on silica (dichloromethane/ethyl acetate 85/15), 9 g of the expected product in the form of an oil were obtained and it had a Rf (dichloromethane-ethyl acetate 85/15)=0.20

IR (CHCl₃) 3340 (—NH—) 1754 (C=O) 1628 (N=CH—N) 1344, 1148 (SO₂). NMR (CDCl₃) 1.37 (t, J=7, CO₂CH₂CH₃); 2.78 and 2.79 (2S, dimethylamine); 2.21 (mobile NH); 3.94 and 4.06 (NCH₂—C=, AB system); 4.35 (q, J=7, CO₂CH₂CH₃); 4.35 (masked N—CH—C≡N); 7.14 (s, N=CH—N); 7.22 (dd, 1H, aromatic); 7.51 (m, 2H, aromatics); 7.39 (s, aromatics).

STAGE D: ethyl cyano-[[[2'-[[[(dimethylamino)-methylene]-amino]-sulfonyl]-(1,1'-biphenyl)-4-yl]-methyl]-(1-oxopentyl)-amino]acetate 5.53 g of potassium carbonate and 3.33 ml of valeryl chloride were added to a solution of 1 g of the product of Stage C in 200 ml of dry acetone. After stirring for 20 hours at ambient temperature, the solution was filtered and dried. Purification was carried out by chromatography with dichloromethane-ethyl acetate 85–15 to obtain 11.6 g of the expected product as a white solid with a Rf (dichloromethane-ethyl acetate 85–15)=0.24

STAGE E: ethyl 3-amino-2-[[[2'-[[[(dimethylamino)-methylene]-amino]-sulfonyl]-(1,1'-biphenyl)-4-yl]-methyl]-(1-oxopentyl)-amino]-3-(methylthio)-2-propenoate 250 mg of the product of Stage D above, 2.5 ml of ethanol and 7 µl of diethylamine were mixed together and the mixture was cooled to −5° C. Methanethiol was bubbled through for 10 minutes and the reaction medium was stirred at −5° C. for one hour, left to return to ambient temperature and stirred for 48 hours. Nitrogen was bubbled through for one hour at ambient temperature and the solvents were eliminated under reduced pressure. After chromatography on silica, (eluant: dichloromethane-ethyl acetate 80–20), 0.91 g of the expected product were obtained.

STAGE F: ethyl 2-butyl-4-(methylthio)-1-[[2'-[[[(dimethyl-amino) methylene]-amino]-sulfonyl]-(1,1'-biphenyl)-4-yl]-methyl]-1H-imidazole-5-carboxylate 50 mg of the product of Stage E, 500 ml of toluene, and a catalytic quantity of amberlyst 15 were mixed together and the mixture was refluxed for 20 hours. The amberlyst was filtered off, followed by washing. The solvents were eliminated under reduced pressure to obtain 0.20 g of the expected product.

STAGE G: ethyl 2-butyl-4-(methylthio)-1-[[2'-[[[amino]-sulfonyl]-(1,1'-biphenyl)-4-yl]-methyl]-1H-imidazole-5-carboxylate A solution of 43.5 g of the product of Stage F, in 800-ml of methanol and 400 ml of concentrated hydrochloric acid was refluxed for 3 hours. The methanol was evaporated off and the remaining phase was adjusted to pH of 5–6 by the addition of 6N sodium hydroxide. Extraction was carried out three times with 400 ml of ether. The extracts were dried on Na₂SO₄ and then the solvent was evaporated to obtain 37.5 g of crude product which was impasted in a mixture of 50 ml of ethanol and 500 ml of isopropyl ether, then filtered to obtain 31.4 g of the expected product as a white solid melting at 127°–129° C.

STAGE H: ethyl 2-butyl-4-(methylthio)-1-[[2'-[[[(propylamino)-carbonyl]-amino]-sulfonyl]-(1,1'-biphenyl)-4-yl]-methyl]-1H-imidazole-5-carboxylate A solution of 10 g of the product of Stage G, 5.6 g of potassium carbonate (ground up beforehand and dried under reduced pressure at 100° C.) in 70 ml of dimethyl ether of ethylene glycol was refluxed under an inert atmosphere for 2 hours. After one hour, 4 ml of n-propyl isocyanate were added and heating was continued for 30 minutes. The reaction mixture was allowed to return to ambient temperature and then the solvent was evaporated. 100 ml of water were added to the residue and then the pH was adjusted to 5–6 by the slow addition of 1N hydrochloric acid. The product crystallized and was crystallized from 50 ml of ethyl acetate to obtain 10.1 g of the expected product.

STAGE I: 2-butyl-4-(methylthio)-1-[[2'-[[[(propylamino)-carbonyl]-amino]-sulfonyl]-(1,1'-biphenyl)-4-yl]-methyl]-1H-imidazole-5-carboxylic-acid di-potassium salt 2.3 ml of a 6N solution of potassium hydroxide were added at 0° C. to a solution of 2 g of the product of Stage H in 40 ml of ethanol and the reaction medium was allowed to return to ambient temperature. After 72 hours, the precipitate was separated and washed with 4 ml of ethanol, then with 4 ml of ethyl acetate to obtain after drying, 2.04 g of the desired product melting at >260° C.

Analysis: $C_{26}H_{30}K_2N_4O_5S_2$

|  | C | H | N | S |
|---|---|---|---|---|
| % calculated | 50.30 | 4.87 | 9.02 | 10.33 |
| % found | 50.5 | 4.9 | 9.0 | 10.3 |

EXAMPLE 2: 2-butyl4-(methylthio)1-[[2'-[[[(propylamino)carbonyl]amino]sulfonyl](1,1'-biphenyl)4-yl]methyl]1 H-imidazole 5-carboxylic acid di-potassium salt 1) ethyl cyano-[[[2'-[[[(dimethylamino)methylene]amino]sulfonyl](1,1'-biphenyl)4-yl]methyl]amino]acetate 2 g of ethyl mono (4-methylbenzenesulfonate) aminocyano acetate of Stage B of Example 1 and 1.9 g of N-[(dimethylamino) methylene]-4'-formyl-(1,1'-biphenyl)-2-sulfonamide of Stage A of Example 1 were stirred in dichloromethane at 35° for 3 hours and then 0.396 g of sodium cyano borohydride were added. The solution was stirred at ambient temperature for 18 hours and the reaction mixture was filtered, washed with water and evaporated. After chromatography on silica (dichloromethane-ethyl acetate 85-15), 770 mg of the expected product were obtained, identical to that of Stage C of Example 1.

2) The operation was then proceeded with as in Example 1 replacing the product of Stage C of Example 1 with the product above to obtain the expected product, 2-butyl 4-(methylthio) 1-[[2'[[[(propylamino)carbonyl]amino]sulfonyl](1,1'-biphenyl)4-yl]methyl]1H-imidazole 5-carboxylic acid di-potassium salt.

EXAMPLE 3: 2-butyl-4-(methylthio)-1-[[2'-((((propylamino)-carbonyl)-amino)-sulfonyl)-1,1'(biphenyl)-4-yl]-methyl]-1H-imidazole-5-carboxylic acid di-potassium salt

STAGE A: ethyl[[[2'-(aminosulfonyl)-(1,1'-biphenyl)-4-yl]-methyl]-(1-oxopentyl)-amino]-cyanoacetate 1.0 g of the product of Stage D of Example 1 in 20 ml of dimethyl ether of ethylene glycol and 10 ml of concentrated hydrochloric acid were stirred for 30 minutes at 100° C. and after cooling to ambient temperature, the pH of the solution was adjusted to about 6 by the addition of 6N sodium hydroxide. The solution was extracted with ethyl acetate and the organic phases were washed with water saturated with sodium chloride and dried. Purification was carried out by chromatography (eluant: ethyl acetate-heptane 4-1) to obtain 320 mg of the expected product.

STAGE B: preparation of ethyl-cyano-[[[2'-[[[(propylamino)-carbonyl]-amino]-sulfonyl]-(1,1'-biphenyl)-4-yl]-methyl]-(1-oxopentyl)-amino]-acetate 7.2 g of the product of Stage A, 6.5 g of anhydrous potassium carbonate and 1.48 ml of n-propyl isocyanate were stirred in 180 ml of acetone at reflux for 2 hours 30 minutes. After cooling, the solution was treated with 2N hydrochloric acid and the residue obtained was dissolved in an aqueous mixture of dichloromethane. After extraction with methylene chloride, the extracts were dried and the solvents were eliminated under reduced pressure and the product was crystallized from ethyl acetate to obtain 6.5 g of the expected product as a white solid with a Rf ($SiO_2$, ethyl acetate)=0.48 and melting at 131°–133° C.

STAGE C: ethyl 3-amino-2-[[[2'-[[[(propylamino)-carbonyl]-amino]sulfonyl]-(1,1'-biphenyl)-4-yl]-methyl]-(1-oxopentyl)-amino]-3-(methylthio)-2-propenoate A solution of 8.5 g of the product of Stage B and 2.4 ml of triethylamine in 100 ml of dichloromethane was saturated with methanethiol by sweeping through the stirred solution cooled to −20° C. The temperature was allowed to rise and then the solution was maintained under a nitrogen pressure of 10 bars at 40° C. for 48 hours. After concentration, the residue was purified by chromatography on silica (eluant: dichloromethane-MeOH 20-1) to obtain 8.0 g of the expected product with an Rf ($SiO_2$, dichloromethane-MeOH20-1)=0.39.

STAGE D: ethyl 2-butyl-4-(methylthio)-1-[[2'-[[[(propylamino) carbonyl]-amino]-(1,1'-biphenyl)-4-yl]-methyl]-1H-imidazole-5-carboxylate 180 mg of phosphorous pentachloride were suspended in 16 ml of dichloromethane under an argon atmosphere and after cooling to −78° C., 230 mg of 4-dimethylaminopyridine in solution in 10 ml of anhydrous dichloromethane were added. The mixture was stirred for 10 minutes and a solution of 500 mg of the product of Stage C in 25 ml of dichloromethane was added at −78° C. The mixture was stirred for 18 hours at ambient temperature and the precipitate was filtered off, washed with water and dried. After chromatography on silica (eluant: dichloromethane-MeOH 20-1), 330 mg of crude product were obtained which was crystallized from ethyl acetate/n-heptane to obtain 270 mg of the expected product as a white solid with Rf (SiO₂, ethyl acetate/n-heptane 4-1)=0.42 and melting at 127°–129° C.

STAGE E:
2-butyl-4-(methylthio)-1-[[2'-[[[(propylamino)-carbonyl]-amino]-sulfonyl]-(1,1'-biphenyl)-4-yl]-methyl]-1H-imidazole-5 -carboxylic-acid A solution of 130 mg of the product of Stage D in 10 ml of methanol and 3.1 ml of 2N sodium hydroxide was stirred for 18 hours at ambient temperature. The methanol was evaporated and the remaining aqueous solution was acidified to a pH of about 6 by the addition of 2N hydrochloric acid. The precipitate was filtered off, washed with water and dried under reduced pressure to obtain 115 mg of the expected product melting at 109°–111° C.

STAGE F:
2-butyl-4-(methylthio)-1-[[2'-[[[(propylamino)-carbonyl]-amino]-sulfonyl]-(1,1'-biphenyl)-4-yl]-methyl]-1H-imidazole-5 -carboxylic-acid di-potassium salt By salification of the product of Stage C, with an aqueous potassium hydroxide solution of Example 1, the expected product was obtained.

EXAMPLE 4:
2-butyl-4-(methylthio)-1-[[2'-[[[(propylamino)-carbonyl]-amino]-sulfonyl]-(1,1'-biphenyl)-4-yl]-methyl]-1H-imidazole-5-carboxylic acid di-potassium salt 1) ethyl cyano-[[[2'-[[[(dimethylamino)methylene]amino]sulfonyl](1,1'-biphenyl)4-yl]methyl](1-oxopentyl)amino] acetate 200 mg of the product of Stage C of Example 3 were dissolved in 5 ml of dimethyl ether of ethylene glycol and 1 ml of concentrated sulfuric acid was added at ambient temperature. After stirring for one hour, water was added while cooling in an ice bath. Extraction was carried out with dichloromethane and the organic phases were washed and dried. The solvent was evaporated under reduced pressure to obtain 180 mg of crude product which was crystallized from ethyl acetate to obtain 140 mg of the expected product melting at 130°–132° C.

2) The synthesis was continued as in Example 3, replacing the product of Stage D of Example 3 with the product above to obtain the expected product.

EXAMPLE 5:
2-butyl-4-(methylthio)-1-[[2'-[[[(propylamino)-carbonyl]-amino]-sulfonyl]-(1,1'-biphenyl)-4-yl]-methyl]-1H-imidazole-5-carboxylic acid di-potassium salt STAGE A: ethyl cyano-[[[2'-[[[(propylamino)-carbonyl]-amino]-sulfonyl]-(1,1'-biphenyl)-4-yl]-methyl]-amino]-acetate A solution of 2 g of the product of Example 1 Stage A and 1.83 g of ethyl cyanoamino acetate prepared as in European Patent Application No. 0,465,368 in 40 ml of dichloromethane were stirred at 35° C. for 6 hours. The solution was added to a suspension of 11.55 mmoles of sodium borohydride, 2 ml of glacial acetic acid and 30 ml of dichloromethane at +10° C. The solution was stirred for 16 hours and after water was added, the organic phase was extracted, washed and dried. Then the solvents were evaporated under reduced pressure and chromatography was carried out on silica (eluant: dichloromethane-MeOH 30-1) to obtain 1.8 g of the expected product with a Rf (SiO₂; dichloromethane-MeOH 20-1)=0.39

STAGE B: ethyl cyano-[[[2'-[[[(propylamino)-carbonyl]-amino]-sulfonyl]-(1,1'-biphenyl)-4-yl]-methyl]-(1-oxopentyl)-amino]-acetate 1.7 g of the product of Stage A were dissolved in 50 ml of acetone and 0.79 g of K₂CO₃ and 0.45 ml of valeryl chloride were added. The mixture was stirred for 6 hours at ambient temperature and the insoluble part was filtered. The filtrate was evaporated to dryness, which after purification by chromatography (eluant: dichloromethane-ethyl acetate 4-1) yielded 295 mg of the expected product with a Rf (SiO₂, dichloromethane ethyl acetate 4-1)=0.30.

The synthesis was continued as in Stages C, D, E and F of Example 3 to obtain the expected product.

EXAMPLE 6:
2-butyl-4-(methylthio)-1-[[2'-((((propylamino)-carbonyl)-amino)-sulfonyl)-1,1'(biphenyl)-4-yl]-methyl]-1H-imidazole-5-carboxylic acid di-potassium salt STAGE A: ethyl 3-amino-2-[[[2'-[[[(propylamino)-carbonyl]-amino]-sulfonyl]-(1,1'-biphenyl)-4-yl]-methyl]-(1-thiopentyl)-amino]-3 -(methylthio)-2-propenoate A solution of 1 g of the product of Stage C of Example 3 and 342 mg of Lawesson reagent in 10 ml of anhydrous dimethyl ether of ethylene glycol was stirred at ambient temperature for 2 days. The solution was concentrated under reduced pressure and the residue was taken up in a mixture of dichloromethane-water (1-1). After extraction and washing with water, drying and elimination of the solvents, the remaining oil was purified to obtain 506 mg of the expected product with a Rf (SiO₂ ethyl acetate/n-heptane 4-1)=0.45

STAGE B: ethyl 2-butyl-4-(methylthio)-1-[[2'-[[[(propylamino)-carbonyl]-amino]-sulfonyl]-(1,1'-biphenyl)-4-yl]-methyl]- 1H-imidazole-5-carboxylate A solution of 150 mg of the product of Stage A, 58 μl of dimethyl sulfone in 5 ml of dichloromethane was stirred at reflux for 15 hours. After cooling to ambient temperature, the solution was washed with a saturated solution of sodium chloride, and evaporated to dryness under reduced pressure. After chromatography on silica (eluant: ethyl acetate/n-heptane 2/1), 35 mg of the expected product were obtained.

The synthesis was then continued as in Stages E and F of Example 3 to obtain the expected product.

Various modifications of the products and method of the invention may be made without departing from the spirit or scope thereof and it is to be understood that the invention is intended to be limited only as defined in the appended claims.

What is claimed is:
1. A process for the preparation of a compound of the formula

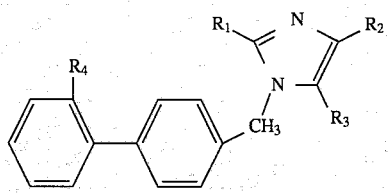

wherein $R_1$ is selected from the group consisting of alkyl, alkenyl, alkynyl and alkylthio of up to 10 carbon atoms and cycloalkyl of 3 to 7 carbon atoms, all optionally substituted with at least one member of the group consisting of phenyl and pyridyl and halogen, $R_2$ and $R_3$ are individually selected from the group consisting of:
a) hydrogen, halogen, —OH, —SH, acyl of an organic carboxylic acid of 1 to 7 carbon atoms, —$NO_2$, —CN, free, salified or esterified carboxy and —$PO_3(R)_2$,
b) —$(CH_2)_{m1}$—$S(O)_{m2}$—X—$R_{10}$,
c) alkyl, alkenyl, alkoxy and optionally oxidized alkylthio of up to 6 carbon atoms optionally interrupted by at least one —O—, —S— or nitrogen and optionally substituted with at least one member of the group consisting of phenyl and pyridyl and halogen,
d) phenyl, benzoyl and optionally oxidized phenylthio, all optionally substituted with at least one member of the group consisting of halogen, alkyl, alkoxy, benzyl and alkoxy carbonyl,
e)

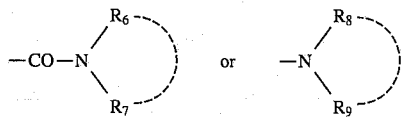

f) —S—S—$R_{12}$,

R is hydrogen or optionally substituted alkyl or phenyl, $m_1$ is an integer from 0 to 4, $m_2$ is an integer from 0 to 2, X is selected from the group consisting of a single bond, —NH—, —NHCO—, —NH—COO—, —N=CH—N—$R_{13}$ and —NHCONH—, $R_{10}$ and $R_{13}$ are individually selected from the group consisting of hydrogen, alkyl and alkenyl of up to 6 carbon atoms, cycloalkyl of 3 to 6 carbon atoms, optionally substituted phenyl and benzyl and benzyl, pyridyl, nitropyridyl, pyrimidyl, tetrazolyl, diazolyl, piperidinyl, alkylpiperidinyl, thiazolyl, alkylthiazolyl, tetrahydrofuranyl and methyltetrahydrofuranyl; $R_6$ and $R_7$ or $R_8$ and $R_9$ are individually selected from the group consisting of hydrogen, amino acids, optionally substituted alkyl and alkenyl of up to 6 carbon atoms, optionally substituted phenyl, benzyl and phenethyl and —$(CH_2)_{m1}$—$S(O)_{m2}$—X—$R_{10}$ or $R_6$ and $R_7$ or $R_8$ and $R_9$ taken together with the nitrogen to which they are attached form a monocyclic ring of 5 to 7 ring members optionally substituted with at least one member of the group consisting of halogen, —OH, —$NO_2$, alkyl and alkoxy of 1 to 6 carbon atoms, —$NH_2$, mono and dialkylamino of 1 to 6 carbon atoms and phenyl or $R_8$ and $R_9$ are individually acyl of an organic carboxylic acid of 1 to 6 carbon atoms or one of $R_8$ and $R_9$ is carbamoyl, alkoxycarbonyl or benzyloxycarbonyl or $R_8$ and $R_9$ together with the nitrogen form phthalimido or succinimido, $R_{12}$ has the definitions of $R_2$ and $R_3$ except for amino or alkoxy with the proviso at least one of $R_2$ and $R_3$ is an optionally substituted alkoxy or —$(CH_2)_{m1}$—$S(O)$—X—$R_{10}$, $R_4$ is selected from the group consisting of —$(CH_2)_{m1}$—$S(O)_{m2}$—X—$R_{10}$ as defined above, halogen, nitro, —$(CH_2)_{m1}$—$COOR_{14}$, —$(CH_2)_{m1}$—$CONHR_{14}$, —$(CH_2)_{m1}$—CN, in which m1 and m2 have the meaning above, —$SO_2$—NH—$SO_2$—$R_{14}$, —NH—$SO_2$—$R_{14}$, —$PO_3$—$R_{14}$, —NH—$SO_2$—$CF_3$ and —$SO_2$—N

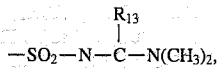

—$(CH_2)_{m1}$—$SO_3R_{14}$, —CO—NH—$OR_{14}$,
—CO—NH—NH—$SO_2$—$CF_3$,
—CO—NH—$SO_2$—$R_{14}$, —$CH_2SO_2NHCO$—$R_{14}$,
—$CH_2CONH$—$SO_2R_{14}$, —$NHSO_2NHCO$—$R_{14}$,
—$NHCONHSO_2$—$R_{14}$,
—$CONHSO_2NR_{14}R_{15}$, —$SO_2NHCONR_{14}R_{15}$,
—$SO_2N(R_{14})OR_{15}$, —$SO_2NHPO(R_{14})_2$, —CONHPO$(R_{14})_2$, —$SO_2NHCN$,
—$SO_2NHCOR_{14}$, —$SO_2NHSO_2NR_{14}R_{15}$,
—$SO_2NHSO_2N(CH_2CH_2)_2Y$,
—$NHSO_2NHSO_2R_{14}$, —$NHSO_2NHPO(R_{14})_2$,
—$NR_{14}COCO_2H$,
—$SO_2NHCO_2R_{14}$, in which $R_{13}$ has the definition above and $R_{14}$ and $R_{15}$ are individually selected from the group consisting of hydrogen alkyl of 1 to 6 carbon atoms, optionally substituted cycloalkyl of 3 to 6 carbon atoms, and Y is oxygen or sulfur; all the alkyl, alkenyl, cycloalkyl, alkylthio, phenylthio, alkoxy, phenyl and benzyl being optionally substituted by at least one member of the group consisting of halogen, hydroxyl, nitro, alkyl, alkenyl and alkoxy of up to 4 carbon atoms, trifluoromethyl, cyano, amino, mono and dialkylamino, free, salified or esterified carboxy, haloalkyl, alkylthio, haloalkylthio, haloalkoxy, phenyl, pyridyl, benzyl, phenethyl, benzoyl, phenoxy, benzyloxy, phenylthio, carbamoyl, acyl, acyloxy and tetrazolyl, the products of Formula I being in all possible racemic, enantiomeric and diastereoisomeric isomer forms, as well as the addition salts with mineral and organic acids or with mineral and organic bases of the said products of formula I comprises reacting a compound of the formula

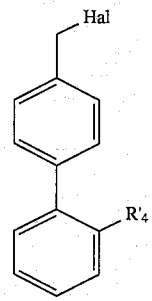

A wherein Hal is halogen and $R'_4$ has the meaning indicated above for $R_4$ in which reactive functions are optionally protected with an oxidizing agent to obtain a compound of the formula

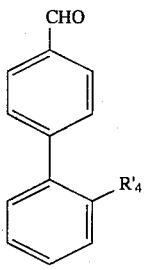   B in which R'$_4$ has the meaning above, reacting the latter with a compound of the formula

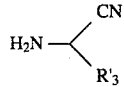   II in which R'$_3$ has the meaning indicated above for R$_3$ in which the optional reactive functions are optionally protected to obtain a product of the formula

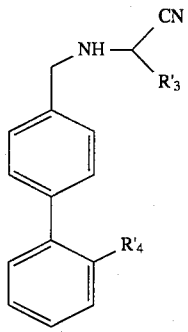   C in which R'$_3$ and R'$_4$ have the meaning above, reacting the latter with a compound of the formula $$R'_1\text{—CO—Hal} \qquad \text{III}$$

in which R'$_1$ has the meaning indicated above for R$_1$ in which the optional reactive functions are optionally protected and Hal is halogen to obtain a product of the formula

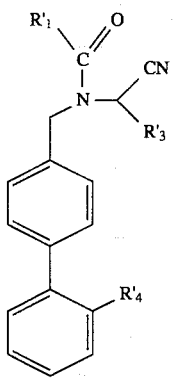   D in which R'$_1$ and R'$_3$ and R'$_4$ have the meanings above, subjecting the latter to an addition reaction on the CN with a reagent capable of introducing R'$_2$ having the meaning above for R$_2$ in which the optional reactive functions are optionally protected to obtain a product of the formula

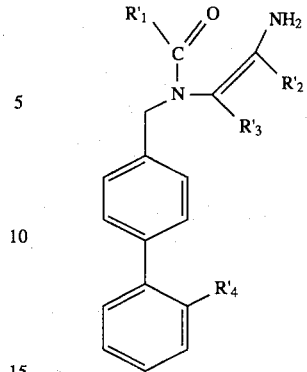   E in which R'$_1$, R'$_2$, R'$_3$ and R'$_4$ have the meanings above, optionally subjecting the latter to a substitution reaction of the oxygen by a sulfur to obtain a product of the formula

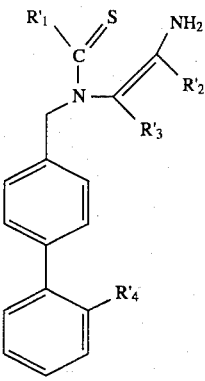   L in which R'$_1$, R'$_2$, R'$_3$ and R'$_4$ have the meanings above, subjecting the product of formula E or the product of formula L to a cyclization reaction to obtain a product of the formula

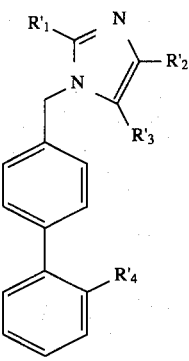   I' in which R'$_1$, R'$_2$, R'$_3$ and R'$_4$ have the meanings above, it being understood that the products of formulae E and L during the above process, and the products of formula I' can optionally be subjected to one or more of the following reactions in any order:

a) an esterification reaction of the acid function,
b) a saponification reaction of the ester function,
c) a conversion reaction of the cyano function into an acid function,
d) a reduction reaction of the carboxy function into an alcohol function,
e) a conversion reaction of the alkoxy function into a hydroxyl function,
f) an oxidation reaction of the group containing a sulfur atom into the corresponding sulfoxide or sulfone, g) a conversion reaction of the alcohol or sulfone function into a corresponding aldehyde or acid function, h) a conversion reaction of the nitrile into tetrazole, i) a conversion reaction of the formyl into a carbamoyl radical, j) a conversion reaction of the carbamoyl into a nitrile, k) a conversion reaction of

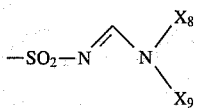

into

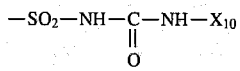

in which $X_8$, $X_9$ and $X_{10}$, individually are hydrogen or alkyl or alkenyl of up to 4 carbon atoms, optionally substituted, or which optionally are subjected to obtain the products of formula I to one or more of the following reactions in any order:

a) an elimination reaction of the protective groups that are carried by the protected reactive functions, b) a salification reaction by a mineral or organic acid or by a base to obtain the corresponding salt, d) a resolution reaction of the racemic forms into resolved products, said products of formula I thus obtained being in all possible racemic, enantiomeric and diastereoisomeric isomer forms.

2. The process of claim 1 for the preparation of a compound of the formula

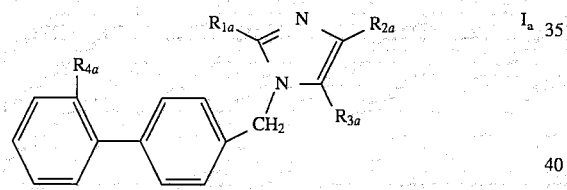

wherein $R'_{1a}$, is alkyl or alkenyl of up to 4 carbon atoms $R_{2a}$ and $R_{3a}$ are individually selected from the group consisting of a) hydrogen, mercapto; formyl; free, salified or esterified carboxy; halogen; hydroxyl; cyano; nitro; acyl;

b) alkyl, alkenyl, alkoxy, optionally oxidized alkylthio of up to 6 carbon atoms, phenyl, benzoyl, phenylthio in which the sulfur atom is optionally mono- or dioxidized, all being optionally substituted by at least one member of the group consisting of halogen, hydroxyl, trifluoromethyl, cyano, nitro, formyl, alkyl and alkoxy of 1 to 4 carbon atoms, phenyl and free, salified or esterified carboxy

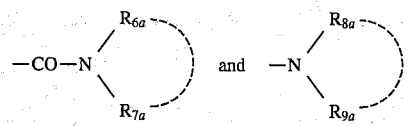

wherein either $R_{6a}$, $R_{7a}$, $R_{8a}$ and $R_{9a}$ are individually selected from group consisting of hydrogen, amino acids, alkyl of 1 to 6 carbon atoms, phenyl, benzyl, phenethyl, or $R_{6a}$ and $R_{7a}$ and $R_{8a}$ and $R_{9a}$ form respectively with the nitrogen atom to which they are linked a heterocyclic selected from the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl, thiomorpholinyl, azepine, indolyl, being optionally substituted by at least one member of the group consisting of halogen, hydroxyl, nitro, alkyl and alkoxy of 1 to 6 carbon atoms and phenyl, $R_{4a}$ is selected from the group consisting of cyano, free, salified or esterified carboxy and $—(CH_2)_p—SO_2—X_a—R_{10a}$ in which p is 0 or 1, $X_a$ is selected from the group consisting of $—NH—$, $—NH—CO—$, $—NH—CO—O—$, $—N=CH—NR_{13a}$, $—NH—CO—NH—$ and a single bond and $R_{10a}$ and $R_{13a}$ are individually selected from the group consisting of hydrogen, alkyl and alkenyl of up to 6 carbon atoms and optionally substituted, pyridyl, phenyl, benzyl, nitropyridyl, pyrimidyl, tetrazolyl, diazolyl, piperidinyl, alkylpiperidinyl, thiazolyl, alkyl-thiazolyl, tetrahydrofuranyl and methyltetrahydrofuranyl; the alkyl and alkenyl being optionally substituted by at least one member of the group consisting of halogen, hydroxyl, nitro, alkyl, alkenyl and alkoxy of up to 4 carbon atoms, trifluoro-methyl, cyano, amino and mono- and dialkylamino, free, salified or esterified carboxy, phenyl, tetrazolyl; the products of formula $I_a$ being in all possible racemic, enantiomeric and diastereoisomeric isomer forms, as well as the addition salts with mineral and organic acids or with mineral and organic bases of the said products of formula $I_a$, wherein for their preparation as defined in claim 1, products of formulae A, II, III and a reagent capable of introducing $R'_2$ are used in which $R'_1$, $R'_2$, $R'_3$ and $R'_4$ have the values indicated above for $R_{1a}$, $R_{2a}$, $R_{3a}$ and $R_{4a}$ respectively in which the reactive functions are optionally protected.

3. The process of claim 1 for the preparation of a product of the formula

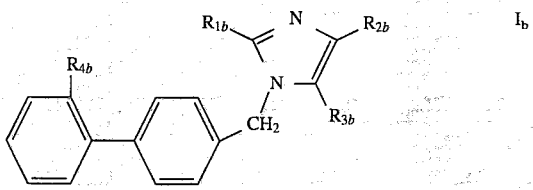

wherein $R_{1b}$ is alkyl of 1 to 4 carbon atoms, $R_{3b}$, is selected from the group consisting of hydrogen, formyl, acyloxy, alkyl and alkoxy optionally substituted or carboxy free, salified or esterified by an alkyl, $R_{2b}$ is selected from the group consisting of an optionally substituted phenylthio, phenylsulfonyl, phenylsulfinyl, alkylthio, alkylsulfonyl or alkylsulfinyl, such that in all those $R_{2b}$ and $R_{3b}$, alkyl and alkoxy of up to 6 carbon atoms, and the phenyl are optionally substituted by at least one member of the group consisting of halogen, hydroxyl, trifluoromethyl, acyloxy, free, salified or esterified carboxy, phenyl, pyridyl, tetrazolyl, alkyl and alkoxy of 1 to 4 carbon atoms and themselves optionally substituted by an alkoxy of 1 to 4 carbon atoms, $R_{4b}$ is selected from the group consisting of cyano, free, salified or esterified carboxy and $—SO_2—X_b—R_{10}$ in which $X_b$ is selected from the group consisting of $—NH—$, $—NH—CO—$, $—NH—CO—O—$, $—N=CH—NR_{13b}$, $—NH—CO—NH—$ and a single bond and $R_{10b}$ and $R_{13b}$ are individually selected from the group consisting of hydrogen, methyl, ethyl, propyl, vinyl, allyl, pyridyl, phenyl, benzyl, nitropyridyl, pyrimidyl, tetrazolyl, diazolyl, piperidinyl, alkylpiperidinyl, thiazolyl, alkylthiazolyl, tetrahydrofuranyl, methyltetrahydrofuranyl, the products of formula $I_b$, being in all possible racemic, enantiomeric and diastereoisomeric isomer forms, as well as the addition salts with mineral and organic acids or with mineral and organic bases of said products of formula $I_b$, wherein for their preparation as defined in claim 1, the products of formulae A, II, III and a reagent capable of introducing $R'_2$ are used in which $R'_1$, $R'_2$, $R'_3$ and $R'_4$ have the values indicated above for $R_{1b}$, $R_{2b}$, $R_{3b}$ and $R_{4b}$ respectively in which the reactive functions are optionally protected.

4. The process of claim 1 for the preparation of a compound of the formula

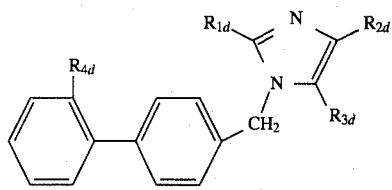

wherein $R_{1d}$ is alkyl of 1 to 4 carbon atoms, $R_{3d}$ is selected from the group consisting of carboxy free, salified or esterified by alkyl of 1 to 4 carbon atoms, acyloxy and alkyl of 1 to 4 carbon atoms optionally substituted by hydroxy, $R_{2d}$ is selected from the group consisting of phenylthio, phenylsulfonyl, phenylsulfinyl, alklythio, alkylsufonyl and alkylsulfinyl, in which the alkyl has 1 to 4 carbon atoms and $R_{4d}$ is selected from the group consisting of —$SO_2$—$NH_2$, $SO_2$—NH—CO—O—$R_{10d}$, —SO—N=CH—$NR_{13d}$ or —$SO_2$—NH—CO—NH—$R_{10d}$ in which $R_{10d}$ and $R_{13d}$ individually selected from the group consisting of hydrogen, methyl, ethyl, n-propyl and propenyl, the products of formula $I_d$ being in all possible racemic, enantiomeric and diastereo-isomeric isomer forms, as well as the addition salts with mineral and organic acids or with mineral and organic bases of said products of formula $I_d$, wherein for their preparation as defined in claim 1, the products of formulae A, II, III and a reagent capable of introducing $R'_2$ are used in which $R'_1$, $R'_2$, $R'_3$ and $R'_4$ have the values indicated above for $R_{1d}$, $R_{2d}$, $R_{3d}$ and $R_{4d}$ respectively in which the reactive functions are optionally protected.

5. The process of claim 1, wherein $R'_4$ is selected from the group consisting of —$SO_2$—$NH_2$, —$SO_2$—NH—CO—O—$R_{10d}$, $SO_2$—N=CH—$NR_{13d}$ and —$SO_2$—NH—CO—NH—$R_{10d}$ in which $R_{10d}$ and $R_{13d}$ are individually selected from the group consisting of hydrogen, methyl, ethyl, n-propyl and propenyl, in which the reactive functions are optionally protected, a product of formula II in which $R'_3$ is selected from the group consisting of carboxy free, salified or esterified by alkyl of 1 to 4 carbon atoms, formyl, acyloxy and alkyl of 1 to 4 carbon atoms optionally substituted by hydroxyl, a product of formula III in which $R'_1$ is alkyl of 1 to 4 carbon atoms, and a reagent capable of introducing $R'_2$ in which $R'_2$ is phenylthio phenylsulfonyl phenylsulfinyl alkylthio, alkylsulfonyl or alkylsulfinyl, in which the alkyl has 1 to 4 carbon atoms, and the reactive functions are optionally protected.

6. The process of claim 1 wherein $R'_4$ is

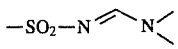

a product of formula II is used in which $R'_3$ is alkoxy or a free, salified or esterified alkoxy or carboxy, a product of formula III is used in which $R'_1$ is alkyl of 1 to 4 carbon atoms and a reagent capable of introducing $R'_2$ in which $R'_2$ is alkylthio or phenylthio optionally oxidized in the form of the sulfoxide or sulfone, the alkoxy, alkylthio and phenylthio being optionally substituted by at least one member of the group consisting of halogen, alkyl and alkoxy of 1 to 4 carbon atoms, trifluoromethyl, amino, mono- or dialkylamino, cyano, phenyl, hydroxyl, free, salified or esterified carboxy, acyl and acyloxy.

7. The process of claim 1 wherein a compound of the formula

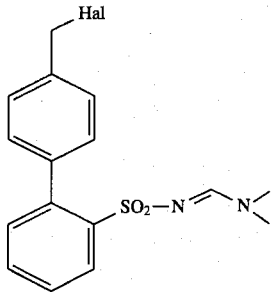

in which Hal is halogen is reacted with an oxidizing agent to obtain a compound of the formula

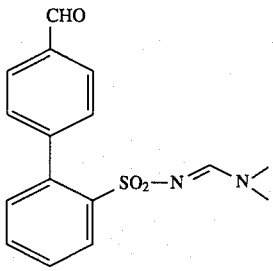

which is reacted with a compound of the formula

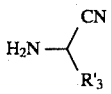

in which $R'_3$ has the meaning above to obtain a product of the formula

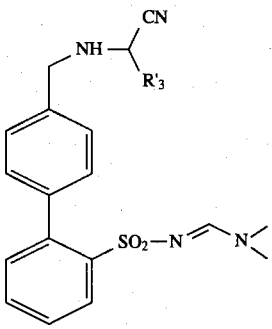

in which $R'_3$ has the meaning above, which is reacted with a compound of the formula $R'_1$—CO—Hal          III in which $R'_1$ and Hal have the meaning above to obtain a product of the formul

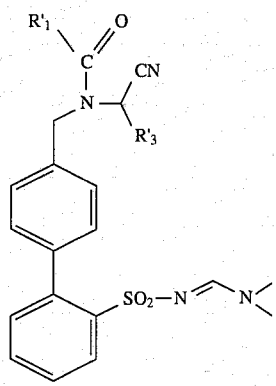

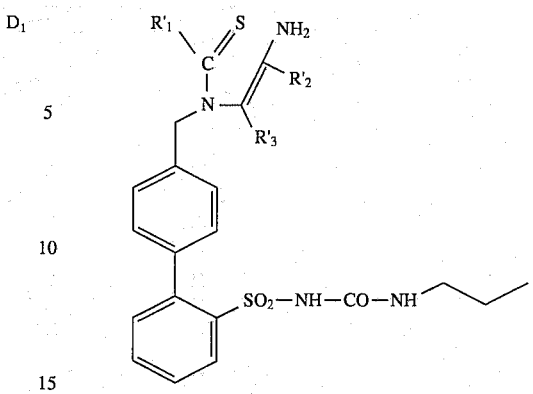

in which R'$_1$ and R'$_3$ have the meanings above, which either is subjected to an addition reaction on the CN using a reagent capable of introducing R'$_2$ as defined above to obtain a product of the formula

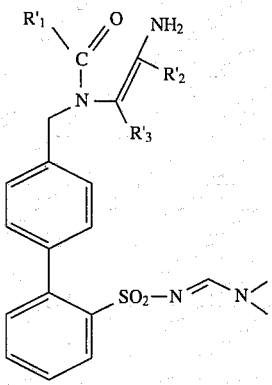

in which R'$_1$, R'$_2$ and R'$_3$ have the meanings above, which is optionally subjected to a substitution reaction of the oxygen of a sulfur to obtain a product of the formula

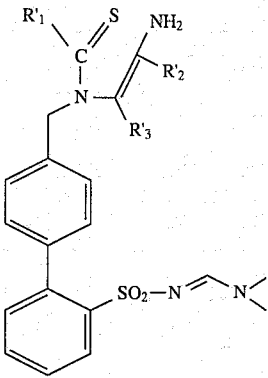

in which R'$_1$, R'$_2$ and R'$_3$ have the meanings above, which optionally is converted into a product of the formula in which R'$_1$, R'$_2$ and R'$_3$ have the meanings above, which product of formula E$_1$, L$_1$ or L$_2$ is subjected to a cyclization reaction to obtain a product of the formula

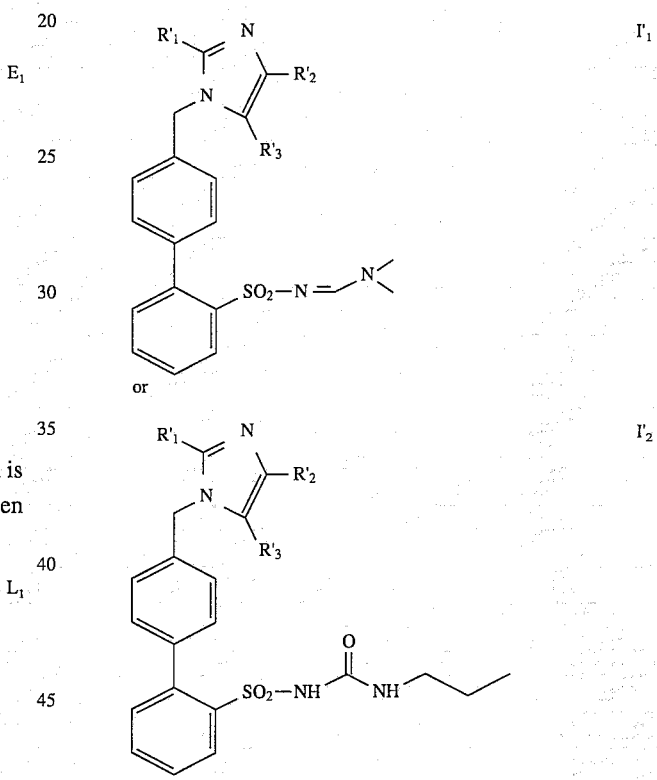

in which R'$_1$, R'$_2$ and R'$_3$ have the meanings above, and optionally the product of formula I'$_1$ is converted into a product of formula I'$_2$ as defined above or the product of formula D$_1$ is subjected to an addition reaction on

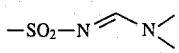

to obtain a product of the formula

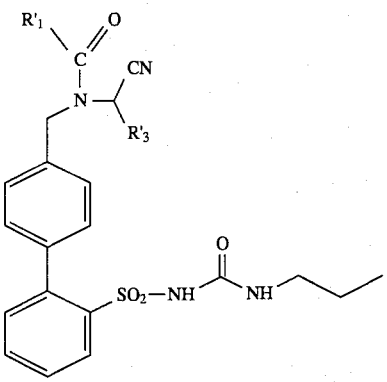

D₂ in which R'₁ and R'₃ have the meanings above, which is subjected to an addition reaction on the CN as indicated above to obtain a product of the formula

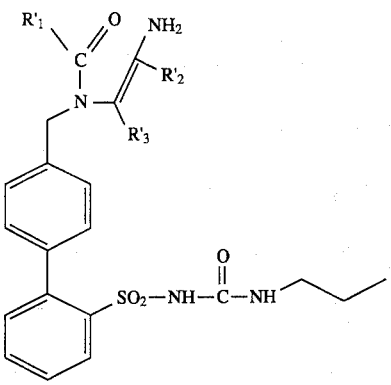

E₂ in which R'₁, R'₂ and R'₃ have the meanings above which is subjected to a cyclization reaction to obtain a product of formula I'₂ as defined above.

8. The process of claim 1 for the preparation of products of formula I selected from the group consisting of
2-butyl-1-[[2'-carboxy-(1,1'-biphenyl)-4-yl]-methyl]-4-(phenylthio)-1H-imidazole-5-carboxylic acid,
2-butyl-1-[[2'-carboxy-(1,1'-biphenyl)-4-yl]-methyl]-4-(methylthio)-1H-imidazole-5-carboxylic acid,
4'-[[2-butyl-4-(ethylthio)-5-(hydroxymethyl)-1H-imidazol-1-yl]-methyl]-(1,1'-biphenyl)-2-carboxylic acid,
2-butyl-1-[[2'-carboxy-(1,1'-biphenyl)-4-yl]-methyl]-4-(ethylsulfonyl)-1H-imidazole-5-carboxylic acid,
2-butyl-1-[[2'-carboxy-(1,1'-biphenyl)-4-yl]-methyl]-4-(ethylsulfinyl)-1H-imidazole-5-carboxylic acid,
2-butyl-1-[[2'-carboxy-(1,1'-biphenyl)-4-yl]-methyl]-4-(ethylthio)-1H-imidazole-5-carboxylic acid,
2-butyl-1-[[2'-carboxy-(1,1'-biphenyl)-4-yl]-methyl]-4-(phenylsulfonyl)-1H-imidazole-5-carboxylic acid,
2-butyl-1-[[2'-carboxy-(1,1'-biphenyl)-4-yl]-methyl]-4-(phenylsulfinyl)-1H-imidazole-5-carboxylic acid,
-2-butyl-1-[[2'-tetrazolyl-(1,1'-biphenyl)-4-yl]-methyl]-4-(methylthio)-1H-imidazole-5-carboxylic acid, 9. The process of claim 1 for the preparation of products of formula I selected from the group consisting of
ethyl 2-butyl-4-(methylthio)-1-[[2'-((((propylamino)-carbonyl)-amino)-sulfonyl)-(1,1'-biphenyl)- 4-yl]-methyl]-1H-imidazole-5-carboxylate,
2-butyl-4-(methylthio)-1-[[2'-((((propylamino)-carbonyl)-amino)-sulfonyl)-( 1,1,-biphenyl)-4-yl]-methyl]-1H-imidazole-5-carboxylic acid,
2-butyl-4-(methylthio)-1-[[2'-((((propylamino)-carbonyl)-amino)-sulfonyl)-(1,1,-biphenyl)-4 -yl]-methyl]-1H-imidazole-5-carboxylic acid,-di-potassium salt.

* * * * *